(12) United States Patent
VanBrocklin et al.

(10) Patent No.: US 8,551,448 B2
(45) Date of Patent: Oct. 8, 2013

(54) ROTANONE ANALOGS: METHOD OF PREPARATION AND USE

(75) Inventors: Henry F. VanBrocklin, Walnut Creek, CA (US); James P. O'Neil, San Leandro, CA (US); Andrew R. Gibbs, Pleasant Hill, CA (US); Nandanan Erathodiyil, Singapore (SG)

(73) Assignee: The Regents of the University of California, Oakland, CA (US)

( * ) Notice: Subject to any disclaimer, the term of this patent is extended or adjusted under 35 U.S.C. 154(b) by 888 days.

(21) Appl. No.: 12/273,509

(22) Filed: Nov. 18, 2008

(65) Prior Publication Data

US 2009/0136424 A1    May 28, 2009

Related U.S. Application Data

(63) Continuation of application No. PCT/US2007/069178, filed on May 17, 2007.

(60) Provisional application No. 60/801,322, filed on May 18, 2006.

(51) Int. Cl.
*A61K 51/04* (2006.01)
*A61K 31/352* (2006.01)
*C07D 311/78* (2006.01)

(52) U.S. Cl.
USPC ........... 424/1.81; 514/453; 549/382; 549/212

(58) Field of Classification Search
USPC .......... 514/453, 184; 549/382, 212; 424/1.65, 424/9.1, 1.81
See application file for complete search history.

(56) References Cited

U.S. PATENT DOCUMENTS

2005/0192458 A1    9/2005    Goodman et al.

FOREIGN PATENT DOCUMENTS

WO            03/086476 A1    10/2003

OTHER PUBLICATIONS

Vanbrocklin, H.F. et al.: Automated HPLC method development of molecular imaging precursors. LCGC North America, Sep. 1, 2005.*

Bhandari, P. et al.: Biosynthesis of rotenone and amorphigenin. Study of the origins of isopropenyl-substituted dihydrofuran E-rings using isotopically labeled late precursors. J. of Chem. Soc., Perkins Transac., vol. 7, pp. 851-863, 1992.*
Marshall, R. C., Leidholdt E. M. Jr., Zhang, D. Y., Barnett, C. A. "Technetium-99m hexakis 2-methoxy-2-isobutyl isonitrile and thallium-201 extraction, washout, and retention at varying coronary flow rates in rabbit heart". Circulation 82: 998-1007 (1990).
Marshall, R. C., Leidholdt E. M. Jr., Zhang, D.Y., Barnett, C. A. "The effect of flow on technetium-99m-teboroxime (SQ30217) and thallium-201 extraction and retention in rabbit heart" J. Nucl. Med. 32: 1979-1988 (1991).
Vanbrocklin HF, Enas JD, Hanrahan SM, Brennan K. M, O'Neil JP, Taylor SE. "[F-18] Fluorodihydrorotenone: Synthesis and evaluation of a mitochondrial electron transport chain (ETC) complex I probe for PET" J. Nucl. Med. 35 (5): 73P (1994).
Marshall, R. C., Powers-Risius, P., Reutter, B. W., Taylor, S. E., VanBrocklin, H. F., Huesman, R. H., Budinger, T. F. "Kinetic analysis of 125I-Iodorotenone as a deposited myocardial flow tracer: comparison with 99mTc-sestamibi" J. Nucl. Med. 42: 272-281 (2001).
Blandini F and Greenamyre JT "Assay of [3H] Dihydrorotenone Binding to Complex I in Intact Human Platelets" Analytical Biochem. 230: 16-19 (1995).
Charalambous A, Manger TJ, Kilbourn MR "Synthesis of (2-[11C] Methoxy) rotenone, a Marker of Mitochondrial Complex I Activity" Nucl. Med. Biol. 22: 65-69 (1995).
O'Neil JP, Marshall RC, Powers-Risius P, VanBrocklin HF "[F-18] Fluororotenoids: Evaluation of Potential Myocardial Imaging Agents in an Isolated, Perfused Rabbit Heart Model" Poster P1 presented to the 19th Annual Western Regional Meeting, Society of Nuclear Medicine, Monterey, CA. Oct. 20-23, 1994.
Vanbrocklin HF, Enas JD, Hanrahan SM, O'Neil JP "Fluorine-18 Labeled Dihydrorotenone Analogs: Preparation and Evaluation of PET Mitochondrial Probes" Journal of Labelled Compounds and Radiopharmaceuticals 37: 217-219 (1995).
Kenski, DM; VanBrocklin, HF; O'Neil, JP "Fluorine-18 Labeled Rotenone Analogs: Preparation and Evaluation of Pet Mitochondrial Probes" J. Labelled Compd. Radiopharm 42, suppl. 1, S333-335 (1999).
International Search Report for Application No. PCT/US2007/069178. Jan. 22, 2008.

* cited by examiner

*Primary Examiner* — Charanjit Aulakh
(74) *Attorney, Agent, or Firm* — Robin C. Chiang; Lawrence Berkeley National Laboratory

(57) ABSTRACT

The present invention provides rotenone analogs and methods of making and using them. Labeled with single photon and positron emitting isotopes, the rotenone analogs of the present invention are useful in, for example, clinical imaging applications as tracers to measure cardiac blood flow and detect regions of ischemia.

40 Claims, 19 Drawing Sheets

| Current Data Parameters | | |
|---|---|---|
| NAME | MJ131C-Z | |
| EXPNO | 4 | |
| PROCNO | 1 | |
| DU | /u | |
| USER | hvh-tbc | |

| F2 - Acquisition Parameters | | |
|---|---|---|
| Date_ | 20060129 | |
| Time | 16.50 | |
| INSTRUM | AV-500 | |
| PROBHD | 5 mm TBI-13C 1 | |
| PULPROG | noesygpph | |
| TD | 4096 | |
| SOLVENT | CDC13 | |
| NS | 4 | |
| DS | 8 | |
| SWH | 4006.410 | |
| FIDRES | 0.978127 | |
| AQ | 0.5113556 | |
| RG | 406.4 | |
| DW | 124.800 | usec |
| DE | 7.11 | usec |
| TE | 292.8 | K |
| d- | 0.00011512 | sec |
| D1 | 2.00000000 | sec |
| D8 | 0.80000001 | sec |
| D16 | 0.00010000 | sec |
| IN0 | 0.00024960 | sec |
| MCREST | 0.00000000 | sec |
| MCWRK | 2.00000000 | sec |
| TAU | 0.39890000 | sec |

| ======== CHANNEL f1 ======== | | |
|---|---|---|
| NUC1 | 1H | |
| P1 | 7.60 | usec |
| P2 | 15.20 | usec |
| PL1 | 0.00 | dB |
| SFO1 | 500.2322510 | MHz |

| ==== GRADIENT CHANNEL ==== | | |
|---|---|---|
| GPNAM1 | SINE.100 | |
| GPNAM2 | SINE.100 | |
| GPX1 | 0.00 | % |
| GPX2 | 0.00 | % |
| GPY1 | 0.00 | % |
| GPY2 | 0.00 | % |
| GPZ1 | 40.00 | % |
| GPZ2 | -40.00 | % |
| P16 | 1000.00 | usec |

| F1 - Acquisition parameters | | |
|---|---|---|
| ND0 | 1 | |
| TD | 256 | |
| SFO1 | 500.2323 | MHz |
| FIDRES | 15.650040 | Hz |
| SW | 8.009 | ppm |
| Fnmode | TPPI | |

| F2 - Processing parameters | | |
|---|---|---|
| SI | 2048 | |
| SF | 500.2300255 | MHz |
| WDW | QSINE | |
| SSB | 2 | |
| LB | 0.00 | Hz |
| GB | 0 | |
| PC | 4.00 | |

| F1 - Processing parameters | | |
|---|---|---|
| SI | 2048 | |
| MC2 | TPPI | |
| SF | 500.2300257 | MHz |
| WDW | QSINE | |
| SSB | 2 | |
| LB | 0.00 | Hz |
| GB | 0 | |

FIG. 15 (CONT.)

Current Data Parameters
NAME         MJ122N-E
EXPNO              4
PROCNO             1
DU                ju
USER         hvh-tbc F2 - Acquisition Parameters
Date_        20060129
Time             16.50
INSTRUM        AV-500
PROBHD   5 mm TBI-13C 1
PULPROG     noesygpph
TD              4096
SOLVENT         CDC13
NS                 2
DS                 8
SWH         4006.410
FIDRES       0.978127
AQ           0.5113556
RG            406.4
DW           124.800     usec
DE              7.11     usec
TE            292.8      K
d-        0.00011512     sec
D1        2.00000000     sec
D8        0.80000001     sec
D16       0.00010000     sec
INO       0.00024960     sec
MCREST    0.00000000     sec
MCWRK     2.00000000     sec
TAU       0.39890000     sec ======== CHANNEL f1 ========
NUC1              1H
P1              7.60     usec
P2             15.20     usec
PL1             0.00     dB
SFO1     500.2322510     MHz ======== GRADIENT CHANNEL ========
GPNAM1        SINE.100
GPNAM2        SINE.100
GPX1            0.00     %
GPX2            0.00     %
GPY1            0.00     %
GPY2            0.00     %
GPZ1           40.00     %
GPZ2          -40.00     %
P16          1000.00     usec F1 - Acquisition parameters
ND0                1
TD               256
SFO1     500.2323040     MHz
FIDRES      15.650040     Hz
SW             8.009     ppm
Fnmode          TPPI F2 - Processing parameters
SI              2048
SF       500.2300255     MHz
WDW            QSINE
SSB                2
LB              0.00     Hz
GB              0
PC              4.00

F1 - Processing parameters
SI              2048
MC2             TPPI
SF       500.2300104     MHz
WDW            QSINE
SSB                2
LB              0.00     Hz
GB              0

FIG. 16 (CONT.)

Planar Images in Canine

Z-Iodorotenone 1h summed 4-4.5 h

E-Iodorotenone 1h summed 4-4.5 h

ROTANONE ANALOGS: METHOD OF PREPARATION AND USE

CROSS-REFERENCE TO RELATED APPLICATIONS

This application claims priority as a continuation application to PCT International Patent Application No. PCT/US2007/069178, filed May 17, 2007, which claims priority to U.S. Provisional Patent Application Ser. No. 60/801,332, filed May 18, 2006; which are hereby incorporated by reference in their entireties.

STATEMENT OF GOVERNMENTAL SUPPORT

This invention was made with government support under Grant (Contract) No. DE-AC03-76F00098 awarded by The United States Department of Energy and Grant No. 5R01EB000482-03 awarded by The United States Department of Health and Human Services. The government has certain rights to this invention.

BACKGROUND OF THE INVENTION

Coronary heart disease (CHD) is the leading cause of death in the United States, accounting for roughly 24% of all deaths. The cost of cardiovascular diseases in 1999 is estimated by the American Heart Association (AHA) at $286.5 billion. Myocardial perfusion scintigraphy is widely used in the evaluation of patients with known or suspected coronary artery disease (CAD). The extensive clinical use of stress myocardial perfusion imaging has resulted largely from its demonstrated improved diagnostic sensitivity and specificity for detection of CAD as compared with exercise electrocardiogram. However, there remains a general need for myocardial flow tracers with improved tracer kinetics.

Although several tracers are currently available for perfusion imaging, all of these tracers suffer from one or more limitations which render them less than ideal agents for assessment of cardiac perfusion (e.g., limited extraction at high flow (Tc99m-sestamibi, T1-201 Chloride) (Marshall et al., 1990), lack of ideal isotope (T1-201 chloride), high liver extraction (Tc99m-teboroxime and Tc99m-sestamibi) (Marshall et al., 1991).

Myocardial perfusion tracers are needed with: improved extraction on first pass; better linearity with true blood flow; improved detection of myocardial viability; and reduced accumulation in non cardiac tissues. Generally, radiopharmaceuticals may be used as diagnostic or therapeutic agents by virtue of the physical properties of their constituent radionuclides. Thus, their utility is not based on any pharmacologic action. Most clinically used drugs of this class are diagnostic agents incorporating a gamma-emitting nuclide which, because of physical or metabolic properties of its coordinated ligands, localizes in a specific organ after intravenous injection. The resultant images can reflect organ structure or function. In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

Rotenone, [2R,6aS,12aS]-1,2,12,12a-tetrahydro-8,9-dimethoxy-2-(1-methylethenyl)-[1]benzopyrano[3,4-b]furo[2,3-h]benzopyran-6(6aH)-one, is a natural product of the Leguminosae plant family and has been used as an insecticide, pesticide and fish poison, and has been used in mitochondrial energy metabolism studies. Rotenone binds on the ND-1 gene product and inhibit Complex I in a reversible competitive manner resulting in the biological effect.

Rotenone has a high affinity for mitochondria. The myocardium is an organ rich in mitochrondria. Novel radiolabeled rotenone analogs that display efficient myocardial uptake and adequate myocardial retention are attractive candidates for clinical evaluation of myocardial blood flow. Rotenone is a specific, high-affinity inhibitor of Complex I (NADH: ubiquinone oxidoreductase), the proximal enzyme of the mitochondrial electron transport chain. Since rotenone inhibition defines the activity of Complex I, defects in radiotracer binding can be expected to reflect functional changes in the enzyme, and hence, abnormalities of the mitochondrial energy metabolism. The prior art rotenone radionuclides utilize a rotenone compound having the following structure:

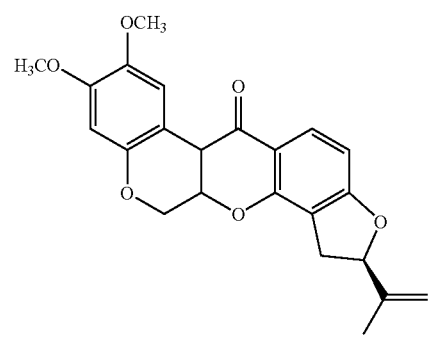 [SMILES: C=C(C)[C@H]1Cc2c(ccc3c2OC2COc4cc(OC)c(OC)cc4C2C3=O)O1]

Labeled rotenone studies have focused on brain and heart imaging (organs enriched with mitochondria) using tritium, carbon-11, fluorine-18, and iodine-125 isotopes (see Van-Brocklin et al., 1994; Marshall et al., 2001; Blandini and Greenamyre, 1995; Charalambous et al., 1995; O'Neil et al., 1994; VanBrocklin et al., 1995; Kenski et al., 1999). Studies on iodine-125 labeled rotenone in isolated blood perfused rabbit heart, a unique model for evaluating myocardial imaging agents, have demonstrated extraction superior to that of Tc-99m sestamibi (0.84±0.05 compared to 0.48±0.10) (Marshall et al., 2001). It also was found to have greater net heart retention than that of Tc-99m sestamibi at 1 min (0.77±0.08 vs. 0.41±0.11) and at 26 min (0.46±0.13 vs. 0.27±0.11) and better correlation with true flow.

SUMMARY OF THE INVENTION

The present invention provides rotenone analogs and methods of using them. In one embodiment of the present invention there is disclosed a compound having the following structure:

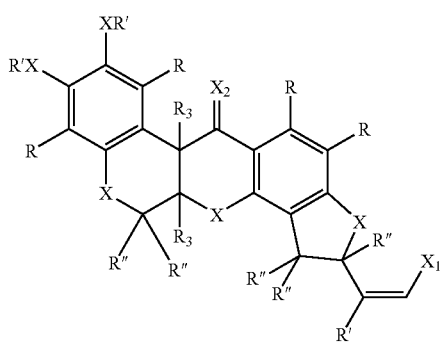

wherein X is independently the same or different and is selected from the group consisting of O and S; $X_1$ is selected from the group consisting of $SnMe_3$, $SnBu_3$, $B(—OCH_2C(CH_3)_2CH_2O—)$, $BF_3K$, ZnI, ZnBr, Br, Cl, F, $CH_2F$, $CH_2CH_2F$, $C_6H_4F$, and $CH_2C_6H_4F$; $X_2$ is selected from the group consisting of O and S; R is independently the same or different and is selected from the group consisting of H, lower alkyl, and a halogen; and R' is independently the same or different and is a lower alkyl; and R" is independently the same or different and is selected from the group consisting of H and a lower alkyl; and $R^3$ is independently the same or different and is selected from the group consisting of H, lower alkyl, and $CH_2F$; and wherein the stereochemical configuration at any stereocenter is R, S or a mixture of these configurations.

In another embodiment of the present invention there is disclosed a compound having the following structure:

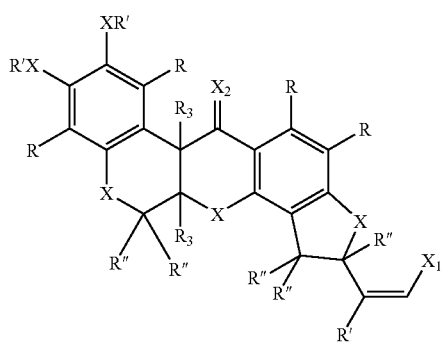

wherein X is independently the same or different and is selected from the group consisting of O and S, and wherein at least one X is S; $X_1$ is selected from the group consisting of $SnMe_3$, $SnBu_3$, $B(—OCH_2C(CH_3)_2CH_2O—)$, $BF_3K$, ZnI, ZnBr, Br, Cl, I, F, $CH_2F$, $CH_2CH_2F$, $C_6H_4F$, and $CH_2C_6H_4F$; $X_2$ is selected from the group consisting of O and S; R is independently the same or different and is selected from the group consisting of H, lower alkyl, and a halogen; and R' is independently the same or different and is a lower alkyl; and R" is independently the same or different and is selected from the group consisting of H and a lower alkyl; and $R^3$ is independently the same or different and is selected from the group consisting of H, lower alkyl, and $CH_2F$; and wherein the stereochemical configuration at any stereocenter is R, S or a mixture of these configurations.

In one embodiment of the present invention there is disclosed a compound having the following structure:

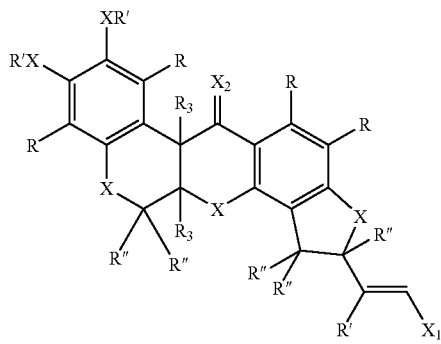

wherein X is independently the same or different and is selected from the group consisting of O and S; $X_1$ is selected from the group consisting of $SnMe_3$, $SnBu_3$, $B(—OCH_2C(CH_3)_2CH_2O—)$, $BF_3K$, ZnI, ZnBr, Br, Cl, I, F, $CH_2F$, $CH_2CH_2F$, $C_6H_4F$, and $CH_2C_6H_4F$; $X_2$ is selected from the group consisting of O and S; R is independently the same or different and is selected from the group consisting of H, lower alkyl, and halogen; R' is independently the same or different and is a lower alkyl; R" is independently the same or different and is selected from the group consisting of H and lower alkyl; and $R_3$ is independently the same or different and is selected from the group consisting of H, lower alkyl, and $CH_2F$; and wherein the stereochemical configuration at any stereocenter is R, S or a mixture of these configurations.

In one embodiment of the present invention there is disclosed a compound having the following structure:

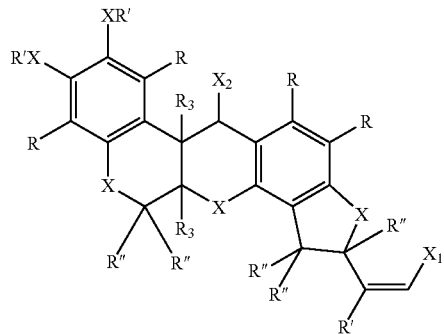

wherein X is independently the same or different and is selected from the group consisting of O and S; $X_1$ is selected from the group consisting of $SnMe_3$, $SnBu_3$, $B(—OCH_2C(CH_3)_2CH_2O—)$, $BF_3K$, ZnI, ZnBr, Br, Cl, F, $CH_2F$, $CH_2CH_2F$, $C_6H_4F$, and $CH_2C_6H_4F$; $X_2$ is selected from the group consisting of OH, OR, OPg, SH, SR, and SPg; R is independently the same or different and is selected from the group consisting of H, lower alkyl, and a halogen; and R' is independently the same or different and is a lower alkyl; and R" is independently the same or different and is selected from the group consisting of H and a lower alkyl; and $R^3$ is independently the same or different and is selected from the group consisting of H, lower alkyl, and $CH_2F$; and wherein the stereochemical configuration at any stereocenter is R, S or a mixture of these configurations.

In another embodiment of the present invention there is disclosed a compound having the following structure:

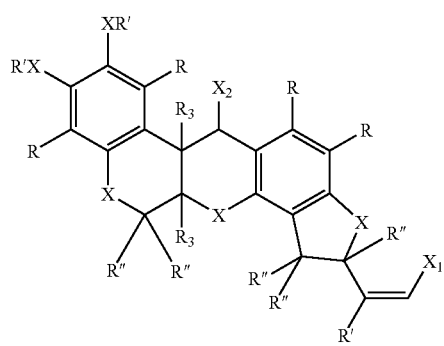

wherein X is independently the same or different and is selected from the group consisting of O and S, and further wherein at least one X is S; $X_1$ is selected from the group consisting of $SnMe_3$, $SnBu_3$, $B(-OCH_2C(CH_3)_2CH_2O-)$, $BF_3K$, $ZnI$, $ZnBr$, Br, Cl, I, F, $CH_2F$, $CH_2CH_2F$, $C_6H_4F$, and $CH_2C_6H_4F$; $X_2$ is selected from the group consisting of OH, OR, OPg, SH, SR, and SPg; R is independently the same or different and is selected from the group consisting of H, lower alkyl, and a halogen; and R' is independently the same or different and is a lower alkyl; and R" is independently the same or different and is selected from the group consisting of H and a lower alkyl; and $R^3$ is independently the same or different and is selected from the group consisting of H, lower alkyl, and $CH_2F$; and wherein the stereochemical configuration at any stereocenter is R, S or a mixture of these configurations.

In one embodiment of the present invention there is disclosed a compound having the following structure:

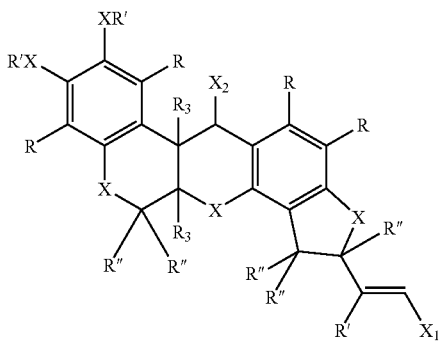

wherein X is independently the same or different and is selected from the group consisting of O and S; $X_1$ is selected from the group consisting of $SnMe_3$, $SnBu_3$, $B(-OCH_2C(CH_3)_2CH_2O-)$, $BF_3K$, $ZnI$, $ZnBr$, Br, Cl, I, F, $CH_2F$, $CH_2CH_2F$, $C_6H_4F$, and $CH_2C_6H_4F$; $X_2$ is selected from the group consisting of OH, OR, OPg, SH, SR, and SPg; R is independently the same or different and is selected from the group consisting of H, lower alkyl, and halogen; R' is independently the same or different and is a lower alkyl; R" is independently the same or different and is selected from the group consisting of H and lower alkyl; and $R_3$ is independently the same or different and is selected from the group consisting of H, lower alkyl, and $CH_2F$; and wherein the stereochemical configuration at any stereocenter is R, S or a mixture of these configurations.

In another embodiment, the present invention provides a compound having the structure:

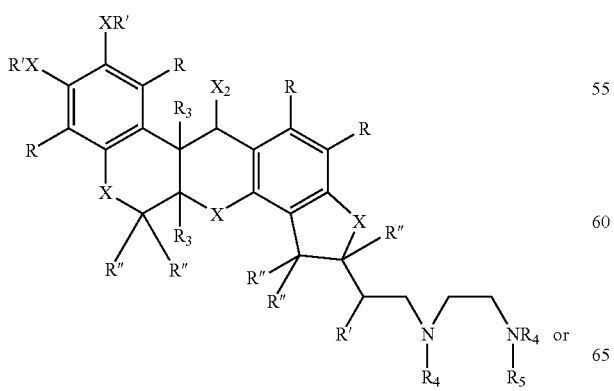

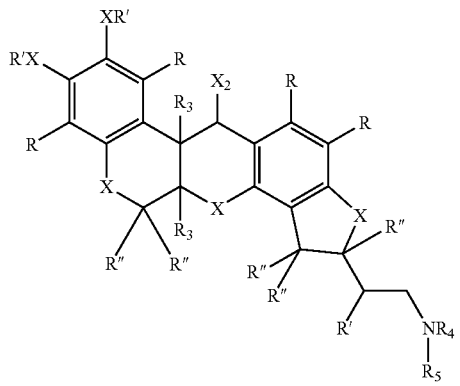

wherein X is independently the same or different and is selected from the group consisting of O and S; $X_2$ is selected from the group consisting of OH, OR, OPg, SH, SR, SPg, =O, and =S; R is independently the same or different and is selected from the group consisting of H, lower alkyl, and halogen; R' is independently the same or different and is a lower alkyl; R" is independently the same or different and is selected from the group consisting of H and lower alkyl; $R_3$ is independently the same or different and is selected from the group consisting of H, lower alkyl, and $CH_2F$; and $R_4$ is independently the same or different and is selected from the group consisting of H, alkyl, and aryl; and $R_5$ is selected from the group consisting of $CH_2CH(OH)CH_2F$, $CH_2C_6H_4F$, $COC_6H_4F$, and $CH_2CH_2F$; and wherein the stereochemical configuration at any stereocenter is R, S or a mixture of these configurations.

In some embodiments, the present invention provides a compound having the structure:

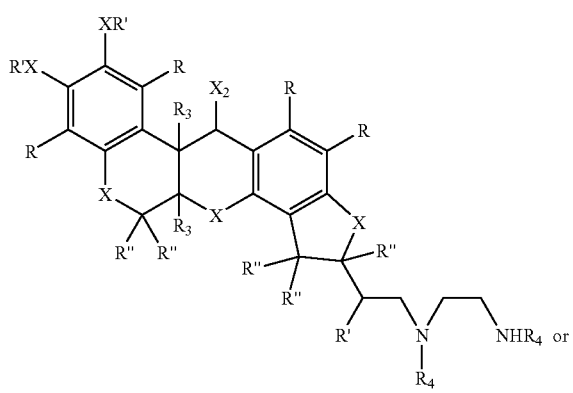

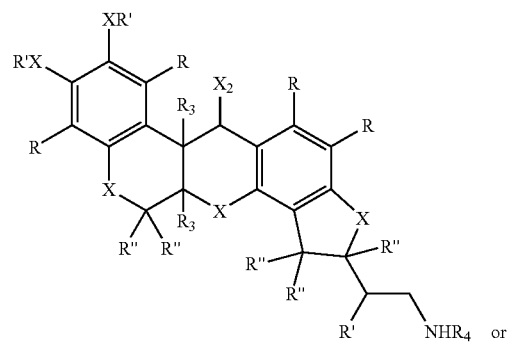

-continued

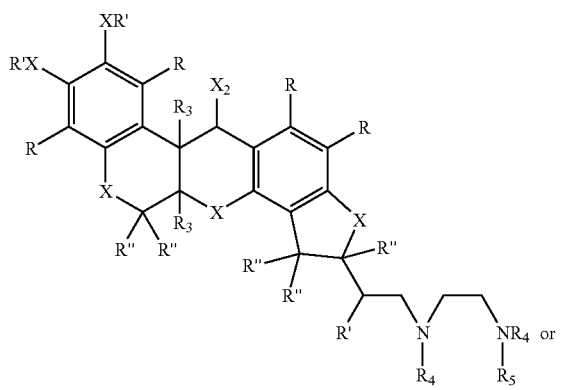

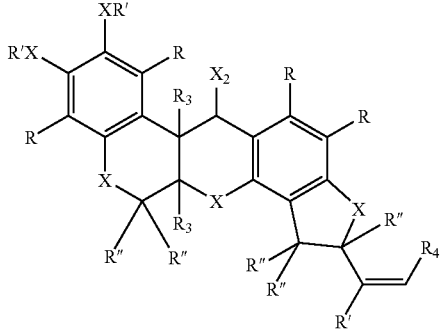

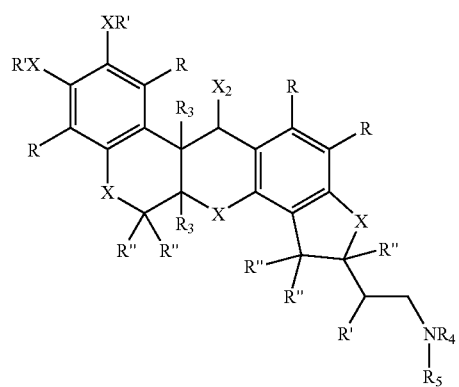

wherein X is independently the same or different and is selected from the group consisting of O and S; $X_2$ is selected from the group consisting of OH, OR, OPg, SH, SR, SPg, =O, and =S; R is independently the same or different and is selected from the group consisting of H, lower alkyl, and halogen; R' is independently the same or different and is a lower alkyl; R" is independently the same or different and is selected from the group consisting of H and lower alkyl; $R_3$ is independently the same or different and is selected from the group consisting of H, lower alkyl, and $CH_2F$; and $R_4$ is independently the same or different and is selected from the group consisting of H, alkyl, and aryl; and $R_5$ is selected from the group consisting of $^{11}CH_3$ and $^{11}CH_3CH_2$; and wherein the stereochemical configuration at any stereocenter is R, S or a mixture of these configurations.

In some embodiments, the present invention provides a compound having the structure:

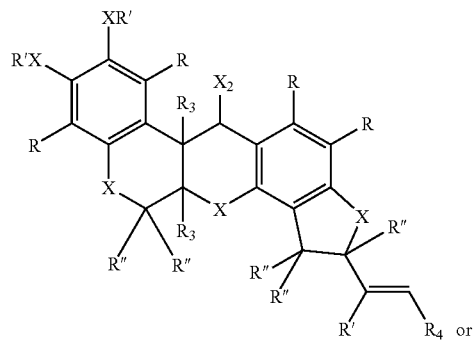

wherein X is independently the same or different and is selected from the group consisting of O and S; $X_2$ is selected from the group consisting of OH, OR, OPg, SH, SR, SPg, =O, and =S; R is independently the same or different and is selected from the group consisting of H, lower alkyl, and halogen; R' is independently the same or different and is a lower alkyl; R" is independently the same or different and is selected from the group consisting of H and lower alkyl; $R_3$ is independently the same or different and is selected from the group consisting of H, lower alkyl, and $CH_2F$; and $R_4$ is selected from the group consisting of $^{11}CH_3$, $^{12}CH_3$, $^{11}CH_3CH_2$, and $^{12}CH_3CH_2$; and wherein the stereochemical configuration at any stereocenter is R, S or a mixture of these configurations.

In one embodiment, the present invention provides a compound having the structure:

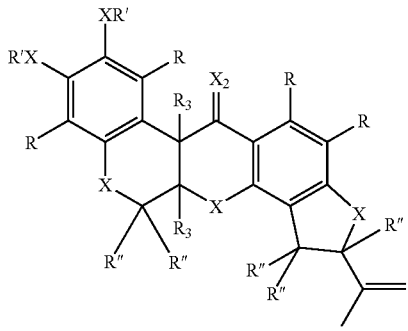

wherein X is independently the same or different and is selected from the group consisting of O and S; $X_2$ is selected from the group consisting of O and S; R is independently the same or different and is selected from the group consisting of H, lower alkyl, and halogen; R' is independently the same or different and is a lower alkyl; R" is independently the same or different and is selected from the group consisting of H and lower alkyl; and $R_3$ is selected from the group consisting of $^{11}CH_3$, $^{11}CH_3CH_2$, and $^{12}CH_3CH_2F$; and wherein the stereochemical configuration at any stereocenter is R, S or a mixture of these configurations.

In certain embodiments, the present invention provides a compound having the structure:

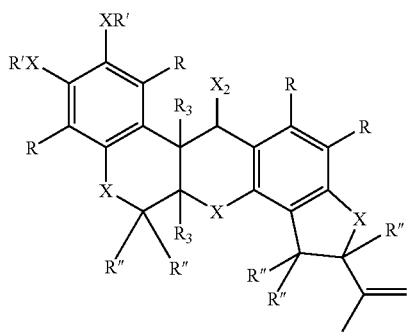

wherein X is independently the same or different and is selected from the group consisting of O and S; $X_2$ is selected from the group consisting of OH, OR, OPg, SH, SR, and SPg; R is independently the same or different and is selected from the group consisting of H, lower alkyl, and halogen; R' is independently the same or different and is a lower alkyl; R" is independently the same or different and is selected from the group consisting of H and lower alkyl; and $R_3$ is selected from the group consisting of $^{11}CH_3$, $^{12}CH_3$, $^{11}CH_3CH_2$, and $^{12}CH_3CH_2$; and wherein the stereochemical configuration at any stereocenter is R, S or a mixture of these configurations.

In some embodiments, the present invention provides a compound having the structure:

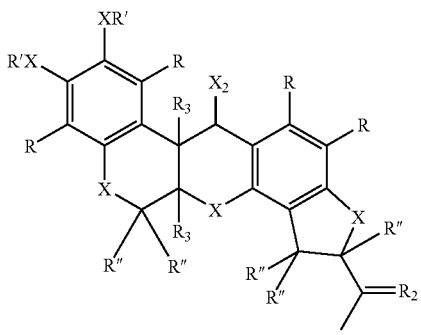

wherein X is independently the same or different and is selected from the group consisting of O and S; $X_2$ is selected from the group consisting of OH, OR, OPg, SH, SR, SPg, =O, and =S; R is independently the same or different and is selected from the group consisting of H, lower alkyl, and halogen; R' is independently the same or different and is a lower alkyl; R" is independently the same or different and is selected from the group consisting of H and lower alkyl; $R_2$ is selected from the group consisting of $^{11}CH_3$, $^{12}CH_3$, $^{11}CH_3CH_2$, and $^{12}CH_3CH_2$; and $R_3$ is independently the same or different and is selected from the group consisting of H, lower alkyl, and $CH_2F$; wherein the stereochemical configuration at any stereocenter of the compound is R, S or a mixture of these configurations.

In certain aspects of the invention, one or more halogen in the compounds disclosed herein may be further defined as a halogen isotope. Examples of halogen isotopes that may be incorporated in the compounds of the present invention include, $^{18}F$, $^{19}F$, $^{35}Cl$, $^{37}Cl$, $^{75}Br$, $^{76}Br$, $^{77}Br$, $^{79}Br$, $^{80}Br$, $^{80m}Br$, $^{81}Br$, $^{120}I$, $^{121}I$, $^{122}I$, $^{123}I$, $^{124}I$, $^{125}I$, $^{127}I$, and $^{131}I$. In some aspects of the invention, one or more carbon in the compounds disclosed herein may be further defined as a carbon isotope, such as $^{12}C$ or $^{11}C$. In some aspects of the invention, one or more Se in the compounds disclosed herein may be further defined as a Se isotope, such as $^{73}Se$ or $^{75}Se$.

In one embodiment, the present invention provides a composition comprising a compound of the present invention and a pharmaceutically acceptable vehicle. In certain aspects of the invention, the composition is an injectable composition. In some embodiments, the vehicle is human serum albumin; aqueous buffer solutions, e.g tris (hydromethyl)aminomethane (and its salts), phosphate, citrate, bicarbonate etc.; alcohols, including ethanol, propylene glycol, etc; sterile water; physiological saline; or balanced ionic solutions containing chloride and or dicarbonate salts or normal blood plasma cations such as calcium, potassium, sodium, and magnesium. In certain embodiments of the present invention, the concentration of a labeled compound as described herein is about 1.0 to 50 millicuries. In some embodiments the concentration is about 1.0 to 10, 10 to 20, 20 to 30, 30 to 40, or 40 to 50 millicuries.

In one embodiment, the present invention provides a kit comprising, in suitable container means, at least one rotenone analog compound of the present invention. The rotenone analog may be provided in the kit as a labeled rotenone analog or it may be provided as an unlabelled intermediate compound. A diagnostic kit of the present invention may comprise, for example, a labeled rotenone analog and a pharmaceutically acceptable vehicle. The kit may have a single container means or it may have distinct container means for each compound. The diagnostic kit may further comprise a syringe or other device for administering a labeled rotenone analog and a pharmaceutically acceptable vehicle to a subject. The diagnostic kit may further comprise instructions for using the components of the kit.

In one embodiment, the present invention provides a method of imaging a region in a patient comprising: (a) administering to a patient a diagnostically effective amount of a composition comprising a labeled rotenone analog and a pharmaceutically effective vehicle; (b) exposing a region of the patient to radiation; and (c) obtaining an image of the region of the patient. In certain aspects of the invention, the region is the heart. In other aspects of the invention the region is the brain. In some embodiments, the composition is administered in a volume of about 1 to 10 mL. In some embodiments, the concentration of the labeled rotenone analog administered to the patient is about 1.0 to 50 millicuries. In some embodiments the concentration is about 1.0 to 10, 10 to 20, 20 to 30, 30 to 40, or 40 to 50 millicuries. In some embodiments, the composition is administered by intraarterial injection or intravenous injection.

In another embodiment, the present invention provides a method of imaging blood flow in a patient comprising: (a) administering to a patient a diagnostically effective amount of a composition comprising a labeled rotenone analog and a pharmaceutically effective vehicle; (b) exposing the patient to radiation; and (c) obtaining an image of the patient. The image may be of the patient's whole body or it may be a region of the patient such as the heart or brain. In some embodiments, the composition is administered in a volume of about 1 to 10 mL. In some embodiments, the concentration of the labeled rotenone analog administered to the patient is about 1.0 to 50 millicuries. In some embodiments the concentration is about 1.0 to 10, 10 to 20, 20 to 30, 30 to 40, or 40 to 50 millicuries. In some embodiments, the composition is administered by intravenous injection.

In other embodiments, the present invention provides methods of synthesizing the rotenone analogs disclosed herein. In particular, the present invention provides methods comprising the steps in the chemical synthesis schemes shown in FIG. 1, FIG. 2, FIG. 3, FIG. 4, FIG. 7, FIG. 8, FIG. 9, FIG. 10, FIG. 11, FIG. 12, FIG. 13, and FIG. 14.

It is contemplated that any method, compound, or composition described herein can be implemented with respect to any other method, compound, or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be readily understood by the following detailed description in conjunction with the accompanying drawings.

DETAILED DESCRIPTION OF THE ILLUSTRATIVE EMBODIMENTS

A. Rotenone Analogs

Figure 1:
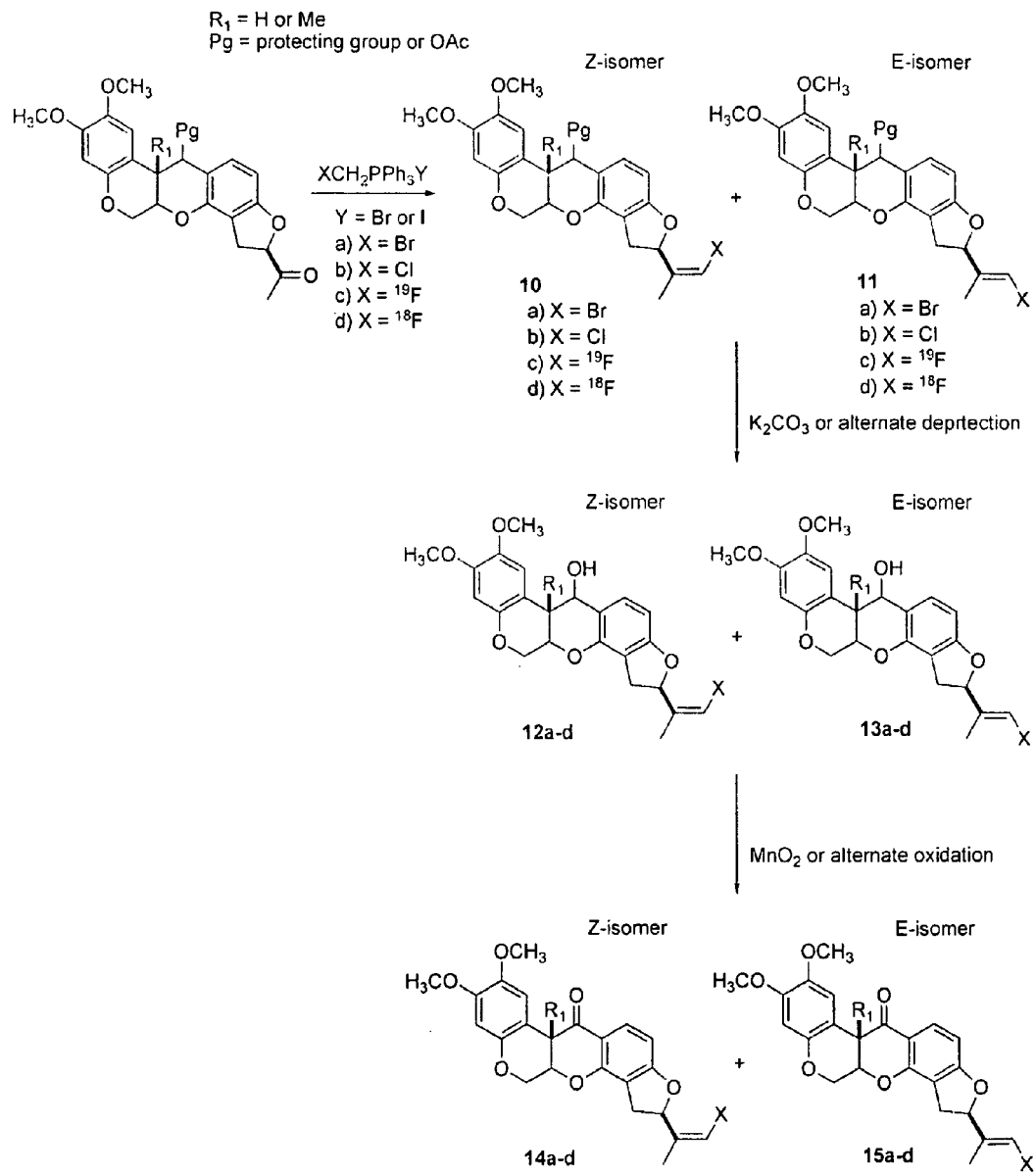
FIG. 1 shows a synthetic pathway in accordance with one embodiment of the present invention for the synthesis of Z and E rotenone isomers.
Figure 2:
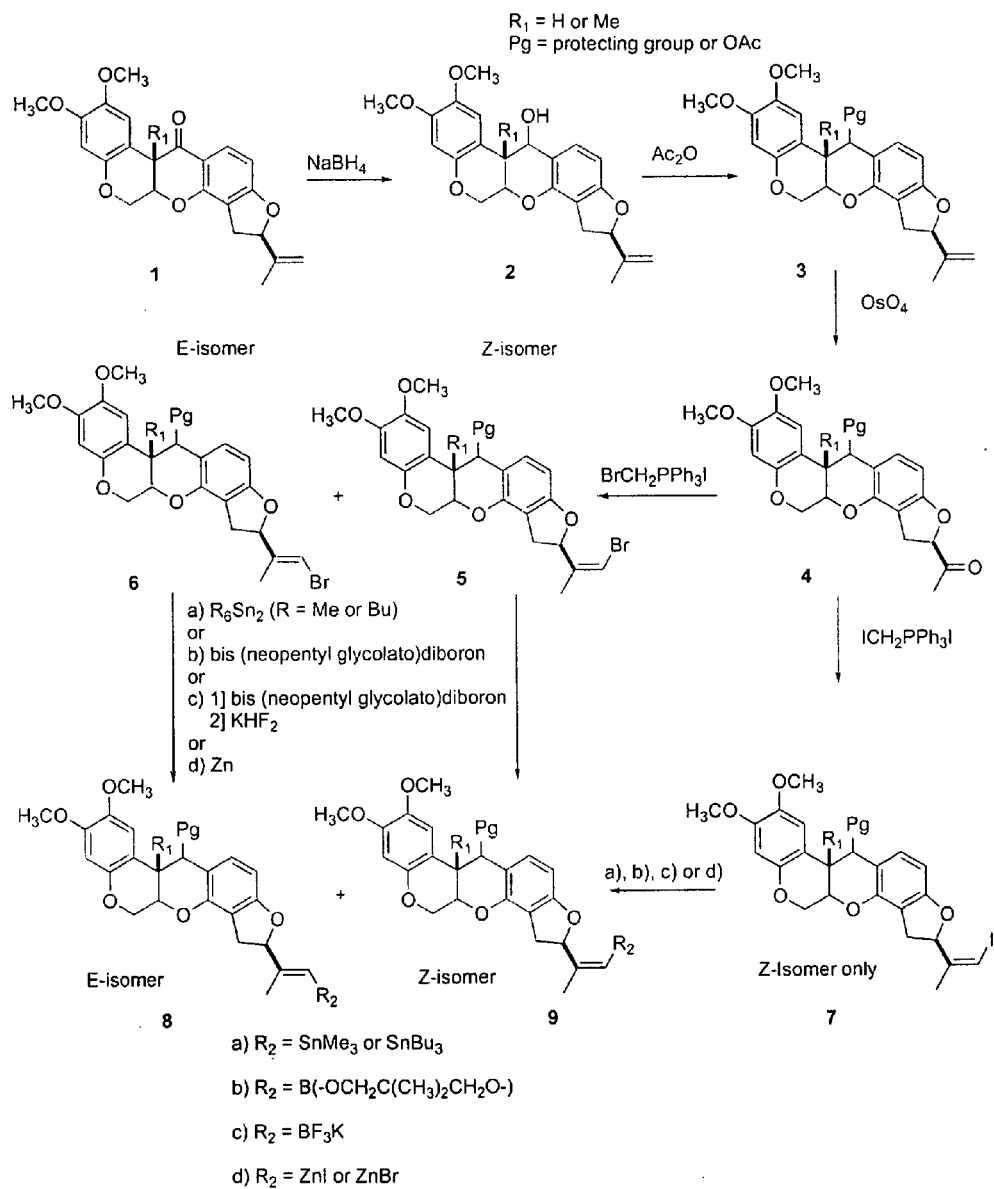
FIG. 2 shows a synthetic pathway in accordance with one embodiment of the present invention for the synthesis of halovinyl intermediates.
Figure 3:
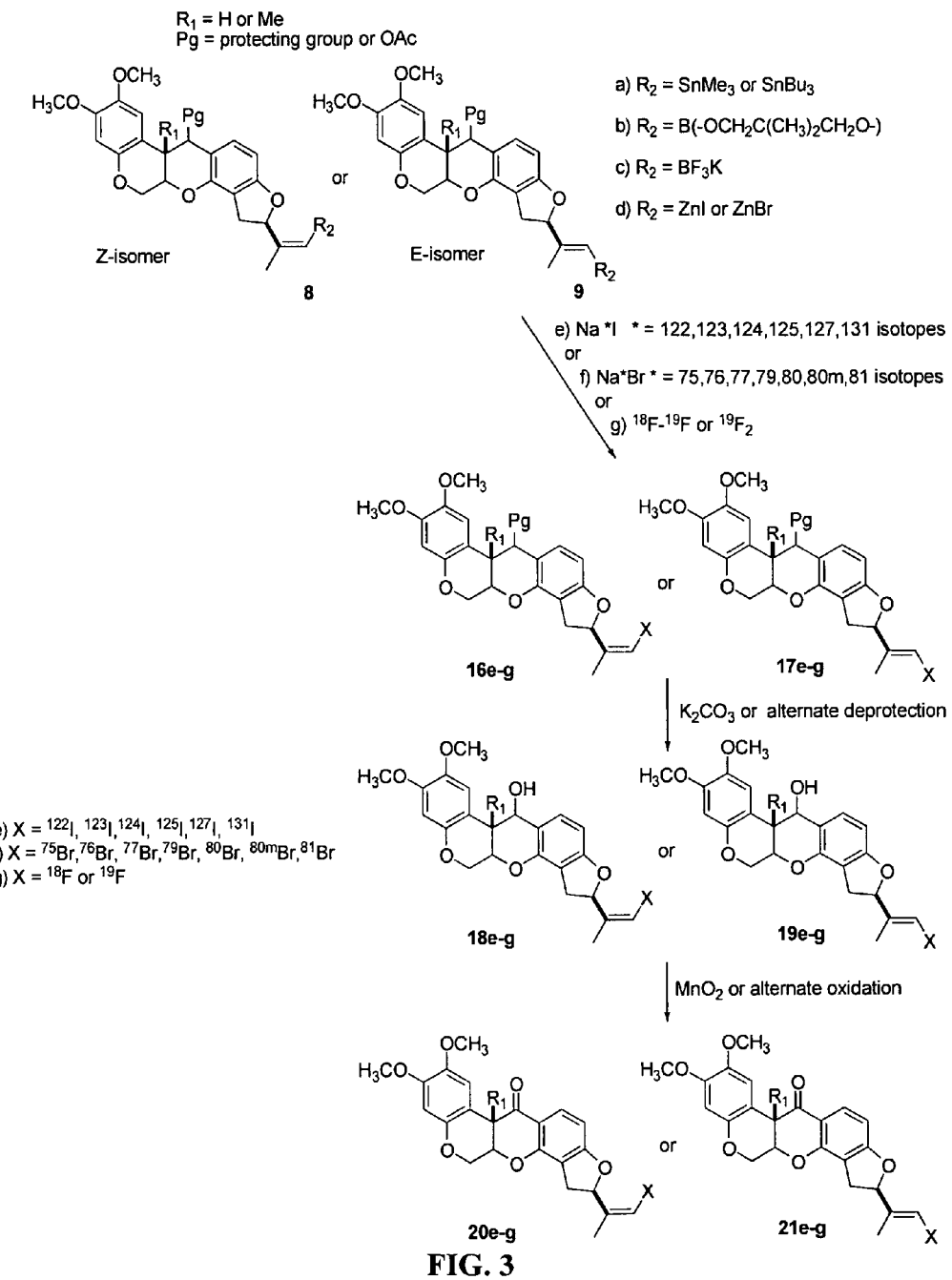
FIG. 3 shows a synthetic pathway in accordance with one embodiment of the present invention for the synthesis of Z and E isomers of the present invention.
Figure 4:
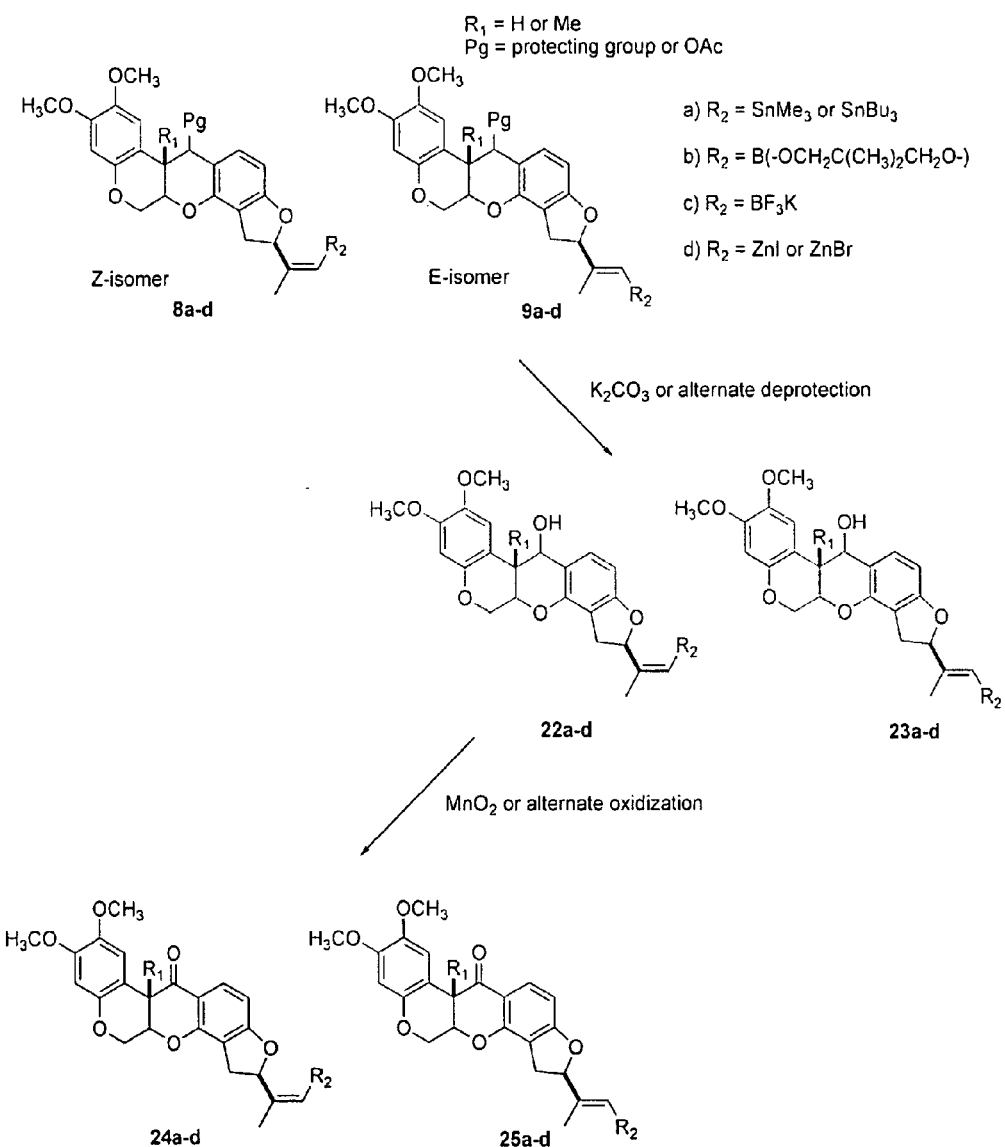
FIG. 4 shows a synthetic pathway in accordance with one embodiment of the present invention for the synthesis of halovinyl intermediates.

The present invention provides novel rotenone analogs and methods for their preparation and use. Rotenone is a natural product of the Leguminosae plant family and has been used as an insecticide, pesticide and fish poison, and has been used in mitochondrial energy metabolism studies. Rotenone is a specific, high-affinity inhibitor of Complex I (NADH: ubiquinone oxidoreductase), the proximal enzyme of the mitochondrial electron transport chain. Since rotenone inhibition defines the activity of Complex I, defects in radiotracer binding can be expected to reflect functional changes in the enzyme, and hence, abnormalities of the mitochondrial energy metabolism.

In certain embodiments, the present invention provides novel rotenone analogs labeled with halogen isotopes or carbon isotopes. Labeled with single photon and positron emitting isotopes, the rotenone analogs of the present invention are useful in, for example, clinical imaging applications as tracers to measure cardiac blood flow and detect regions of ischemia. The rotenone analogs disclosed herein have superior extraction and retention properties to other tracers (e.g., $^{99m}$Tc-sestamibi and $^{99m}$Tc-tetrofosmin) currently in clinical use. Those of ordinary skill in the art will be able to make the rotenone analogs of the present invention in view of the description provided herein and the chemical synthesis schemes shown in FIG. 1, FIG. 2, FIG. 3, FIG. 4, FIG. 7, FIG. 8, FIG. 9, FIG. 10, FIG. 11, FIG. 12, FIG. 13, and FIG. 14.

In certain embodiments of the invention, the rotenone analogs may be labeled with halogen isotopes. Examples of halogen isotopes include, $^{18}$F, $^{19}$F, $^{35}$Cl, $^{37}$Cl, $^{75}$Br, $^{76}$Br, $^{77}$Br, $^{79}$Br, $^{80}$Br, $^{80m}$Br, $^{81}$Br, $^{120}$I, $^{121}$I, $^{122}$I, $^{123}$I, $^{124}$I, $^{125}$I, $^{127}$I, and $^{131}$I. Other isotopes that may be used with the compounds of the present invention include, for example, $^{11}$C, $^{73}$Se, and $^{75}$Se. These are non-limiting examples of isotopes. Those of ordinary skill in the art will be able to select the appropriate isotope for labeling the rotenone analog for use in a particular diagnostic or research application.

The terminal haloolefin group of rotenone is a useful functionality in the design of mechanism based radiotracers. Because the potency of these tracers often depends on the geometry of the olefin, there is considerable interest in developing stereospecific methods for these molecules.

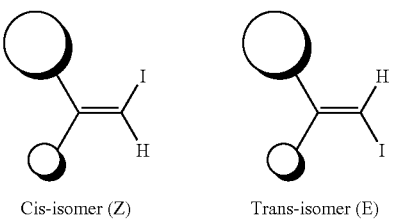

Cis-isomer (Z)    Trans-isomer (E)

A synthetic pathway to the E isomer of [$^{125}$I]iodorotenone was purportedly disclosed in Scheme 1 of Enas et al. (1995). However, as disclosed herein, the synthetic pathway disclosed in Enas et al. actually results in the synthesis of the Z isomer of iodorotenene. Prior to the present invention, a synthetic pathway for producing the E isomer of [$^{125}$I]iodorotenone was not known.

The term "heteroatom" as used herein means an atom of any element other than carbon or hydrogen.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (o) constant. This well known constant is described in many references, for instance, March (1977). The Hammett constant values are generally negative for electron donating groups (C [P]=−0.66 for $NH_2$) and positive for electron withdrawing groups (a [P]=0.78 for a nitro group), a [P] indicating para substitution.

The term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

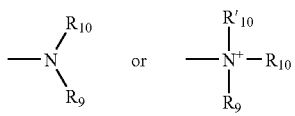

wherein $R_9$, $R_{10}$— and $R'_{10}$ each independently represent a group permitted by the rules of valence.

The term "acylamino" is art-recognized and refers to a moiety that can be represented by the general formula:

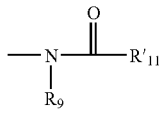

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

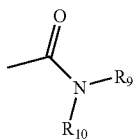

wherein $R_9$ and $R_{10}$ are as defined above.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

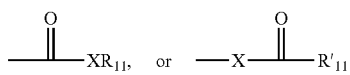

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester". Where X is a sulfur and $R_{11}$ is hydrogen, the formula represents a "thiolcarboxylic acid." Where X is a sulfur and $R'_{11}$ is hydrogen, the formula represents a "thiolformate." On the other hand, where X is a bond, and $R_{11}$ is not hydrogen, the above formula represents a "ketone" group. Where X is a bond, and R is hydrogen, the above formula represents an "aldehyde" group.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl, —O—$(CH_2)_m$—$R_8$, where m and $R_8$ are described above.

The term "sulfonate" is art recognized and includes a moiety that can be represented by the general formula:

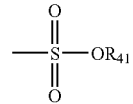

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations, the contents of which are hereby incorporated by reference in its entirety for all purposes.

The term "sulfate" is art recognized and includes a moiety that can be represented by the general formula:

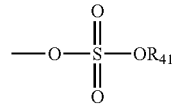

in which $R_{41}$ is as defined above.

The term "sulfonylamino" is art recognized and includes a moiety that can be represented by the general formula:

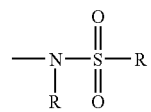

The term "sulfamoyl" is art-recognized and includes a moiety that can be represented by the general formula:

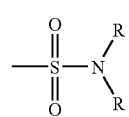

The term "sulfonyl", as used herein, refers to a moiety that can be represented by the general formula:

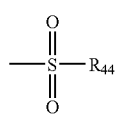

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

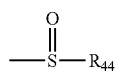

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" ($P_g$) as used herein means temporary substituents which protect a potentially reactive functional group from undesired chemical transformations.

Examples of such protecting groups include esters of carboxylic acids, silyl ethers of alcohols, and acetals and ketals of aldehydes and ketones, respectively. A list of illustrative, but not exhaustive protecting groups is disclosed in Greene abd Wuts (1991), the contents of which are hereby incorporated by reference in its entirety.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

B. Imaging

The present invention also relates to imaging agents containing a radionuclide as described above, in an amount sufficient for imaging, together with a pharmaceutically acceptable vehicle. Imaging agents incorporating a gamma-emitting nuclide which, because of physical or metabolic properties of its coordinated ligands, localize in a specific organ after they are administered to the patient. The resultant images can reflect organ structure or function. In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

The vehicle should be suitable for injection or aspiration. Non-limiting examples of radiological vehicles include, human serum albumin; aqueous buffer solutions, e.g tris (hydromethyl)aminomethane (and its salts), phosphate, citrate, bicarbonate, etc.; alcohols, including ethanol, propylene glycol, etc; sterile water; physiological saline; and balanced ionic solutions containing chloride and or dicarbonate salts or normal blood plasma cations such as calcium, potassium, sodium, and magnesium.

The concentration of the imaging agent according to the present invention in the radiological vehicle should be sufficient to provide satisfactory imaging, for example, when using an aqueous solution, the dosage is about 1.0 to 50 millicuries. The imaging agent should be administered so as to remain in the patient for about 1 to 3 hours, although both longer and shorter time periods are acceptable. Therefore, convenient ampules containing 1 to 10 mL of aqueous solution may be prepared.

Labeled rotenone analogs of the present invention may be used with imaging techniques such as positron emission tomography (PET) and Single Photon Emission Computed Tomography (SPECT). PET imaging is a diagnostic examination that involves the acquisition of physiologic images based on the detection of radiation from the emission of positrons from a radionuclide compound administered to the patient. The radionuclide compound is typically administered via intravenous injection. Different colors or degrees of brightness on a PET image represent different levels of tissue or organ function. SPECT imaging is a three-dimensional technique combined with computer assisted reconstruction of images of organs to reveal both anatomy and function. As with PET imaging, patients undergoing SPECT imaging are administered a radioactive tracer. PET and SPECT images may be used to evaluate a variety of diseases, and are commonly used in the fields of oncology, cardiology, and neurology.

As discussed above, rotenone has high affinity to Complex I of the mitochondrial electron transport chain. Thus, labeled rotenone analogs may be used to investigate abnormalities in mitochondrial function. Such abnormalities may be associated with, for example, ischemia. Due to its affinity for mitochondria, rotenone is particularly well suited for use with tissues rich in mitochondria, such as the myocardium and brain. For example, PET or SPECT scans of the heart using rotenone radionuclides can be used to determine blood flow to the heart muscle and help evaluate signs of coronary artery disease. This information can assist health care providers in the diagnosis, localization, and risk stratification of patients with known or suspected coronary artery disease.

C. Research Applications

The compounds of the present invention are useful as in vitro and in vivo markers of NADH-quinone oxidoreductase (Complex I) of the mitochondria. Complex I is one of three energy-transducing enzyme complexes of the respiratory chain in mitochondria. It is the point of entry for the major fraction of electrons that traverse the respiratory chain eventually resulting in the reduction of oxygen. Mammalian Complex I is composed of 46 subunits and contains noncovalently bound FMN and several iron-sulfur clusters as prosthetic groups.

Several mitochondrial diseases involve structural and functional defects in Complex I. For example, many cases of Leber's hereditary optic neuropathy (LHON) appear to be associated with a defect in Complex I. In addition, it has been observed that rotenone and 1-methyl-4-phenylpyridium (another Complex I inhibitor) produce drug-induced Parkinsonism in rodents and human, which suggests a link between Parkinson's disease and Complex I function. It has also been suggested that Complex I malfunction is involved in the pathogenesis of diabetes. Therefore, the novel rotenone analogs of the present invention provide valuable research tools for the study of Complex I and associated pathologies, including neurodegenerative diseases like Parkinson's disease and Huntington's disease. In particular, the novel rotenone analogs can be used as in vitro, in situ, or in vivo markers of Complex I.

D. Pharmaceutical Formulations

Pharmaceutical Formulations in accordance with certain embodiment of the present invention comprise an effective amount of one or more of the rotenone radionuclides described above and formulated together with one or more pharmaceutically acceptable carriers and/or diluents.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

E. Kits

Any of the compounds and compositions described herein may be comprised in a kit. The kits will thus comprise, in suitable container means, at least one rotenone analog and/or rotenone analog intermediate. The kits will generally include at least one vial, test tube, flask, bottle, syringe or other container, into which a component may be placed, and preferably, suitably aliquoted. Where there is more than one component in the kit, the kit also will generally contain a second, third or other additional container into which the additional components may be separately placed. However, various combinations of components may be comprised in a container. Such kits may be useful in diagnostic and/or research purposes.

A diagnostic kit of the present invention may comprise a labeled rotenone analog and a pharmaceutically acceptable vehicle. In certain embodiments, the diagnostic kit of the present invention may comprise an unlabeled rotenone analog intermediate. The kit may have a single container means or it may have distinct container means for each compound. The diagnostic kit may further comprise a syringe or other device for administering the labeled rotenone analog and a pharmaceutically acceptable vehicle to a subject. The diagnostic kit may further comprise instructions for using the components of the kit.

F. Examples

Commercially available rotenone was subjected to reduction with sodium borohydride to the corresponding alcohol as a single isomer. Alcohol 2 was protected as acetate and using $OsO_4/NaIO_4$, was oxidized to the ketone in good yield. Wittig reaction with the iodomethylylide furnished the trans iodoolefin compound (Z/E ratio, 99:1), which upon hydrolysis with $K_2CO_3$-Methanol system resulted in the iodorotenol as a white crystalline solid. Iodorotenol was transformed into iodorotenone using manganese dioxide oxidation in moderate yield.

Brominated rotenone analogs using the bromomethylylide in the Wittig reaction have been developed. The E and Z isomers of the bromorotenol were separated and the corresponding $^{125}I$ labeled molecules were produced. Wittig reaction of the ketone with bromomethylylide resulted in the formation of the bromoolefin in the ratio of 55:45 favoring the Z-isomer. This upon hydrolysis gave the bromoalcohols, which were separated by preparative HPLC. The E and Z-isomers were converted into the corresponding iodides via stannylation.

All non-aqueous reactions were carried out under an argon or nitrogen atmosphere unless otherwise noted. High-performance liquid chromatography (HPLC) was performed with a Waters Associates HPLC. $^1$H NMR spectra were recorded with either a Brucker 300 or 400 MHz spectrometer with CDCl$_3$ as the internal standard (∂7.26 ppm). Elemental analyses were performed by Microanalytical Laboratory, operated by the College of Chemistry, University of California, Berkeley. High resolution (HRMS) and low resolution (LRMS) mass spectral determinations (EI or FAB) were made at the Center for Mass Spectrometry, University of California, Berkeley.

Figure 5:
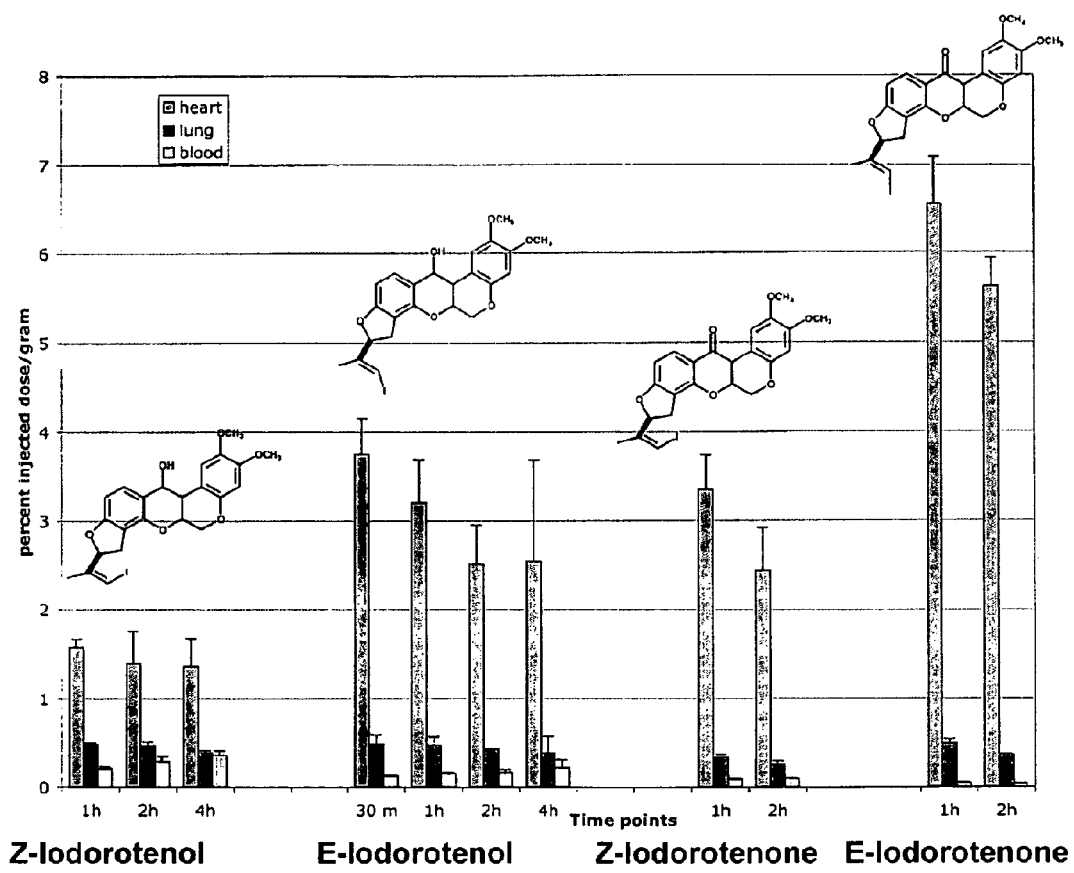
FIG. 5 shows a comparison of the E and Z isomers of iodorotenone analogs in perfusion studies.
Figure 6:
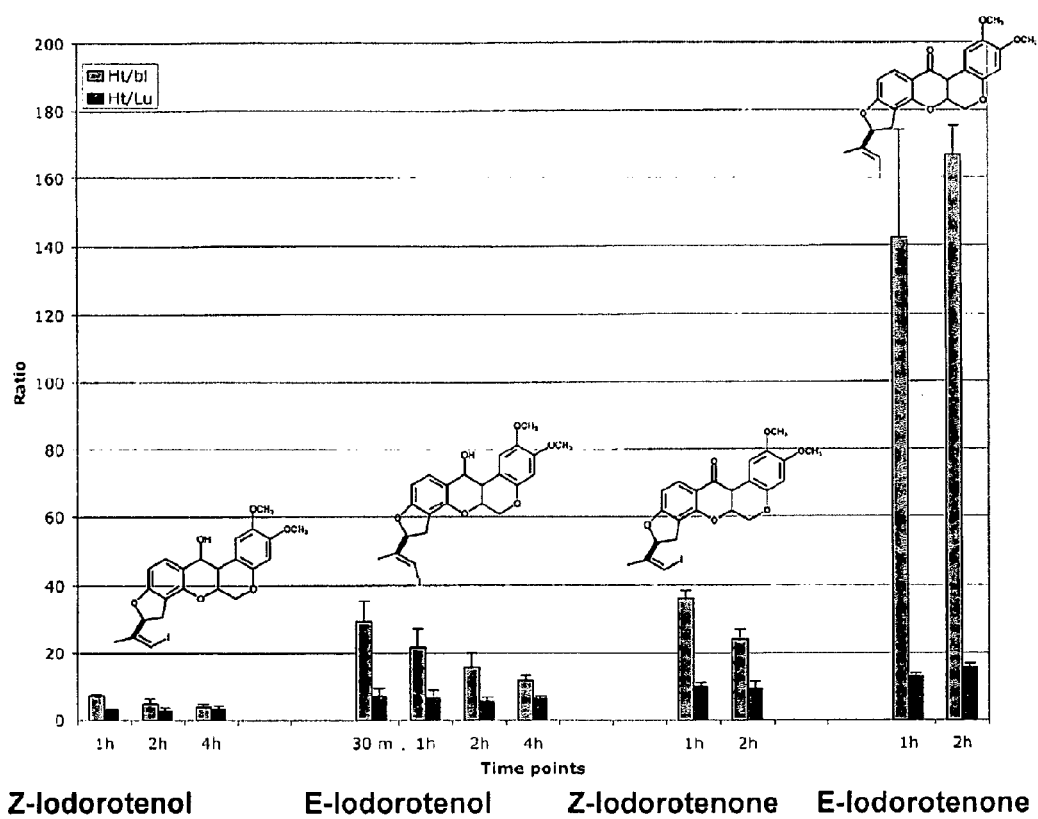
FIG. 6 shows a comparison of the E and Z isomers of iodorotenone anologs in perfusion studies.
Figure 7:
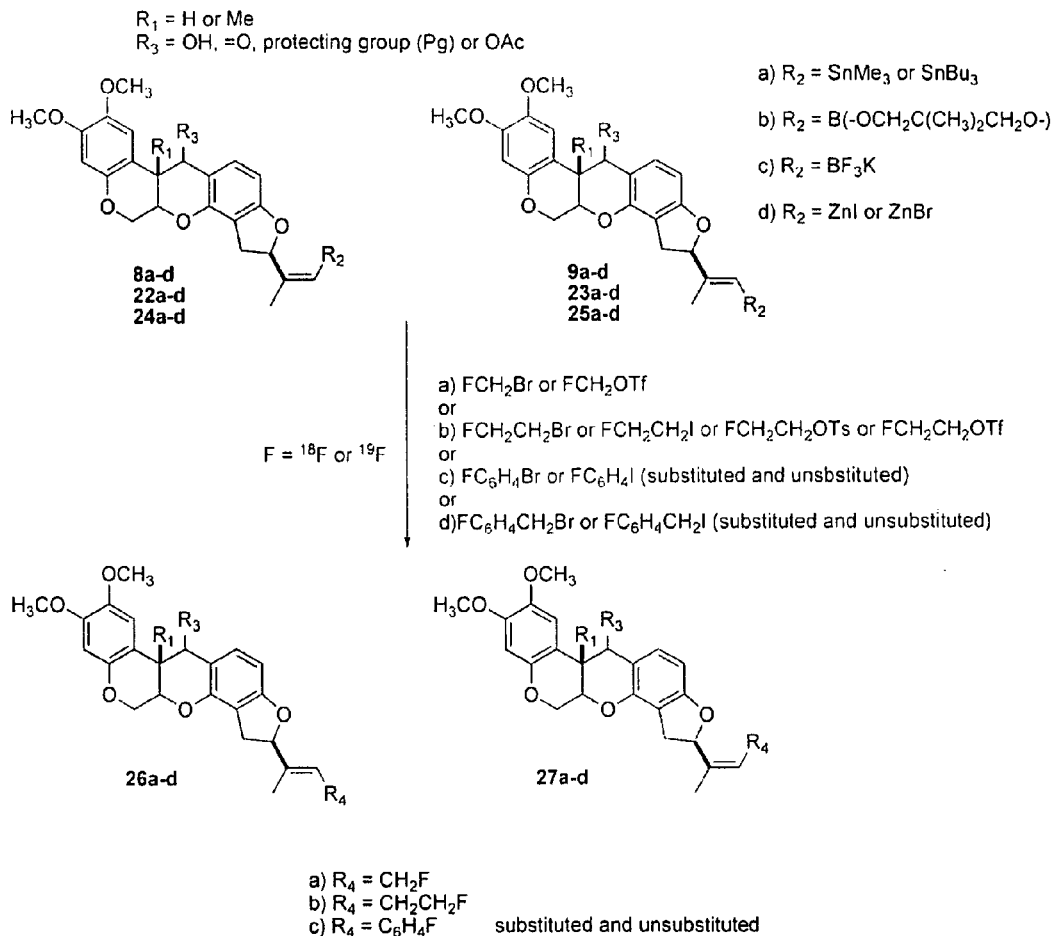
FIG. 7 shows a synthetic pathway in accordance with one embodiment of the present invention for the synthesis of fluorine-labeled rotenone analogs.
Figure 8:
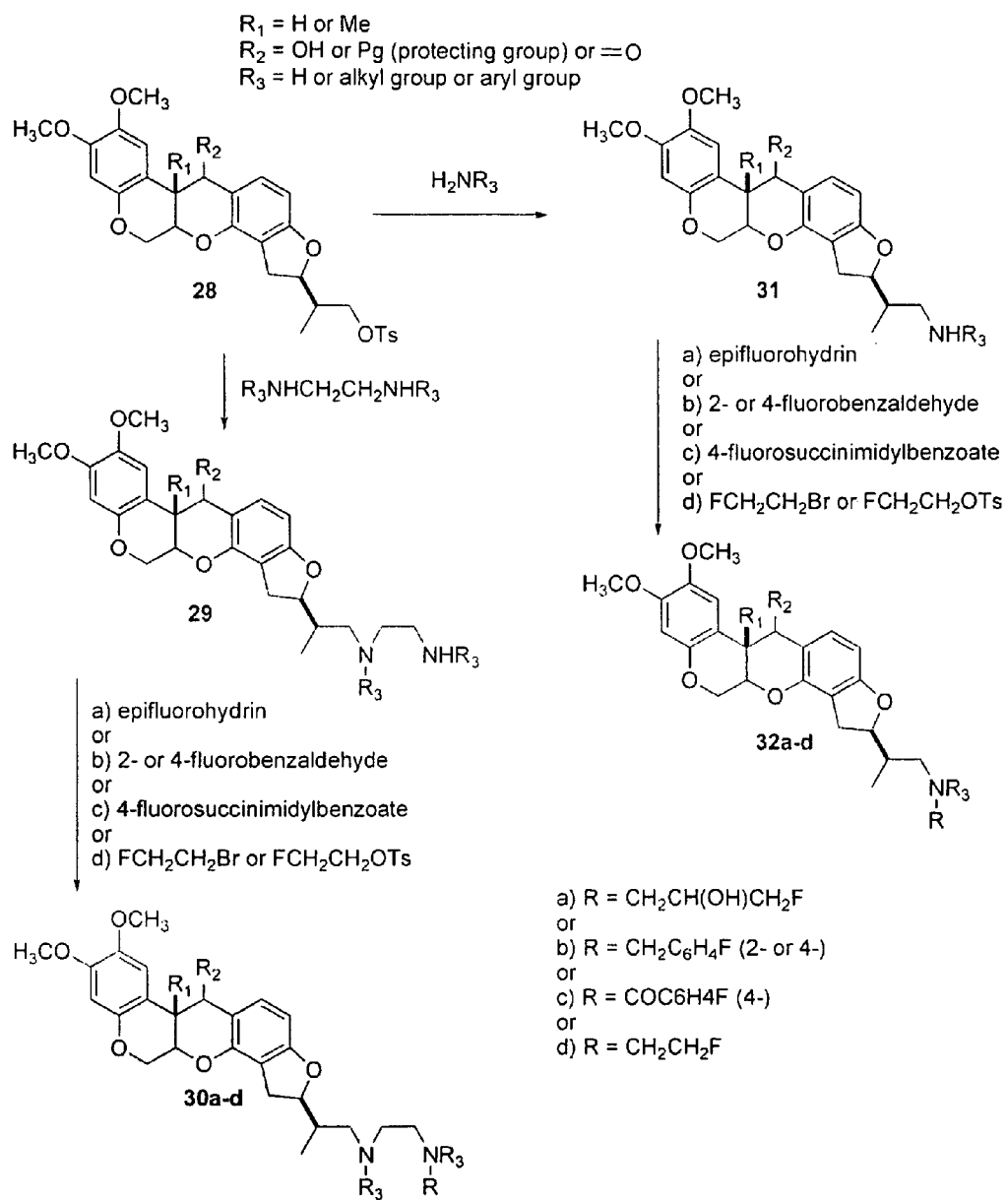
FIG. 8 shows a synthetic pathway in accordance with one embodiment of the present invention for the synthesis of fluorine-labeled rotenone analogs.
Figure 9:
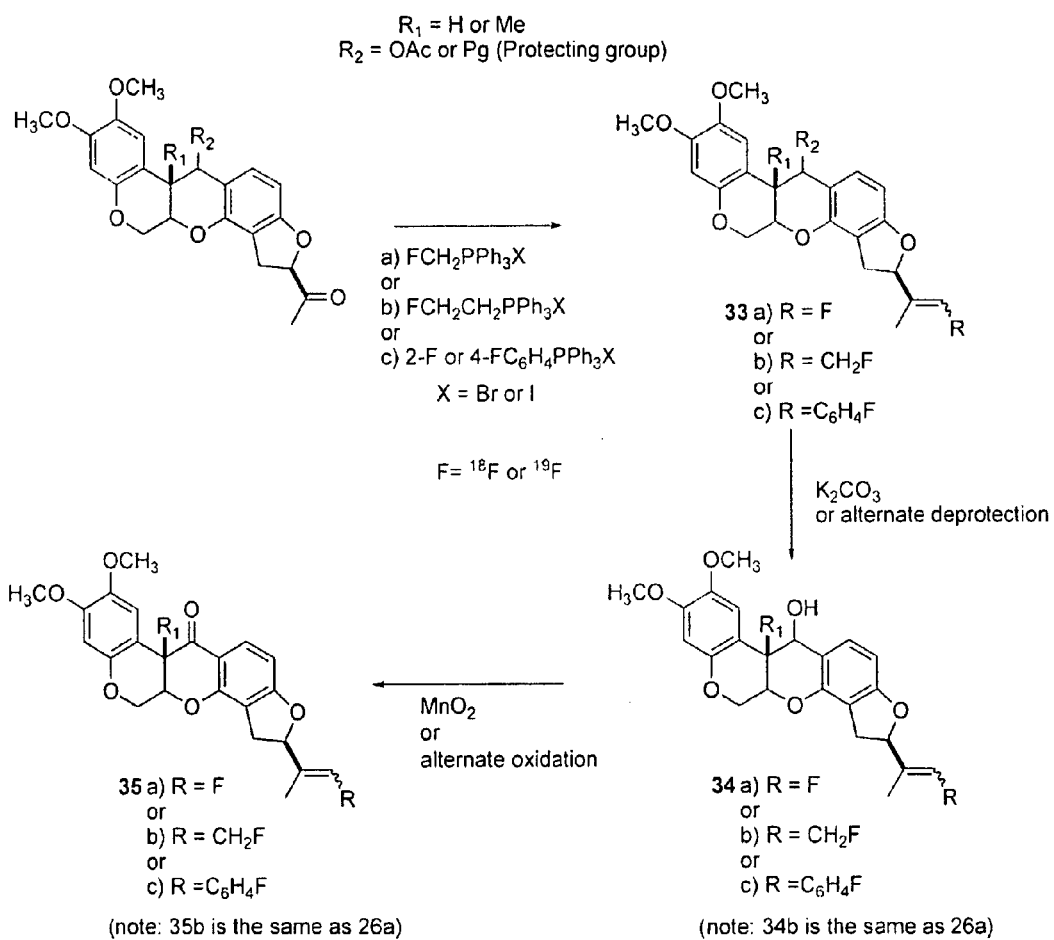
FIG. 9 shows a synthetic pathway in accordance with one embodiment of the present invention for the synthesis of fluorine-labeled rotenone analogs.
Figure 10:
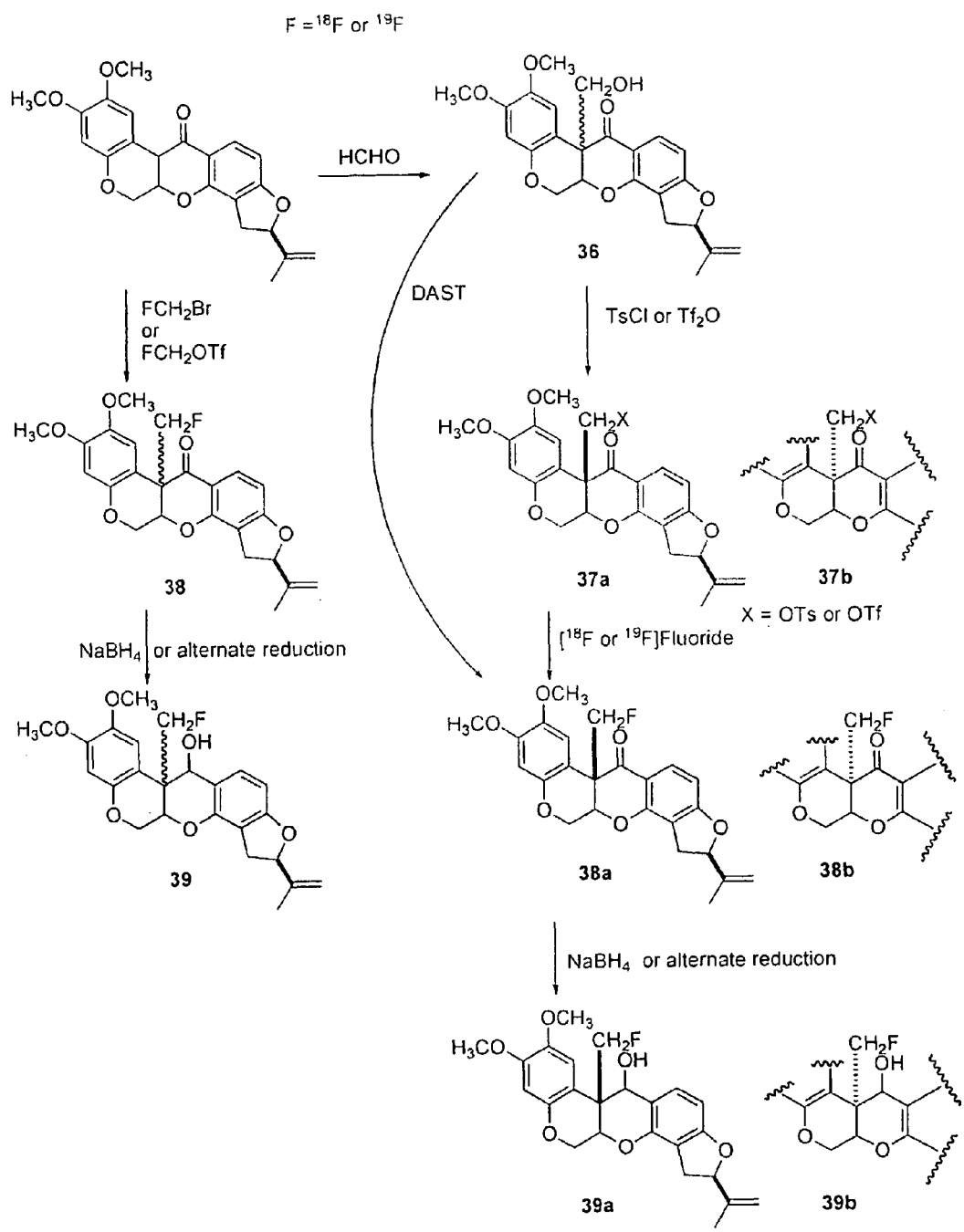
FIG. 10 shows a synthetic pathway in accordance with one embodiment of the present invention for the synthesis of fluorine-labeled rotenone analogs.
Figure 11:
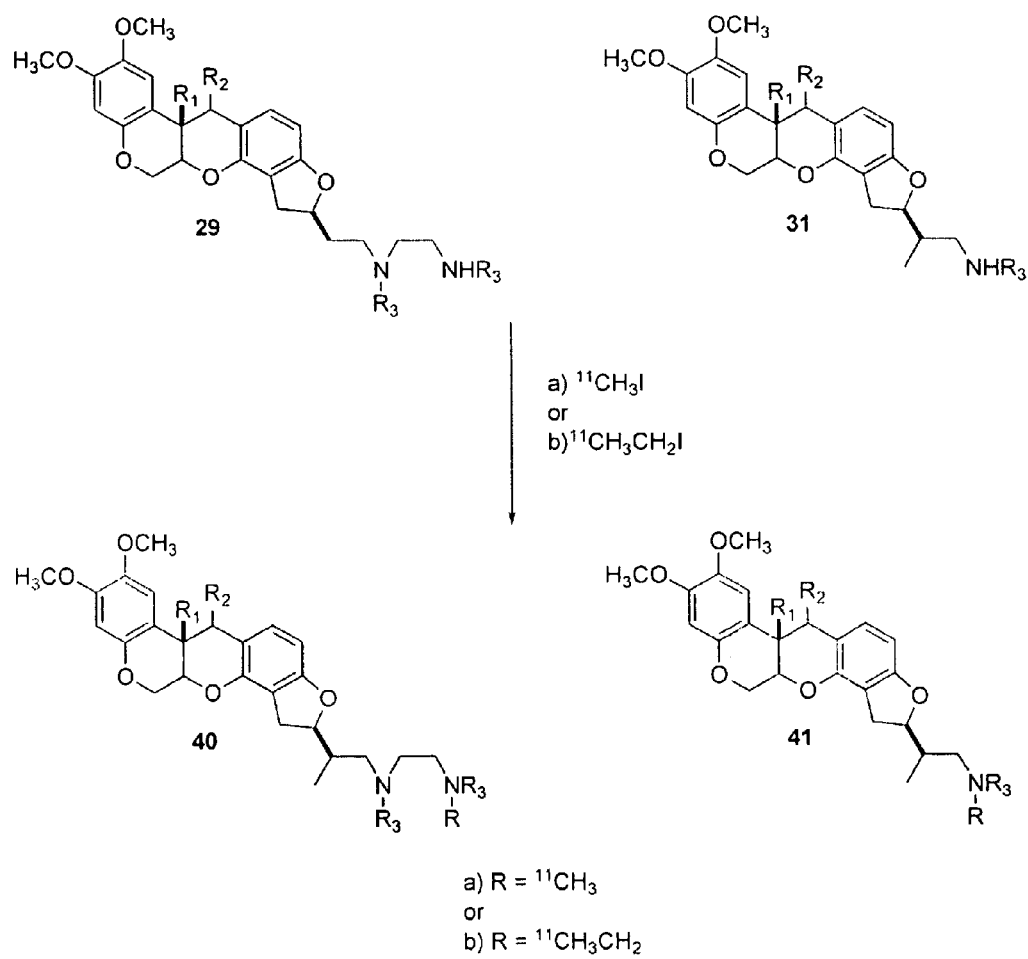
FIG. 11 shows a synthetic pathway in accordance with one embodiment of the present invention for the synthesis of carbon-labeled rotenone analogs.
Figure 12:
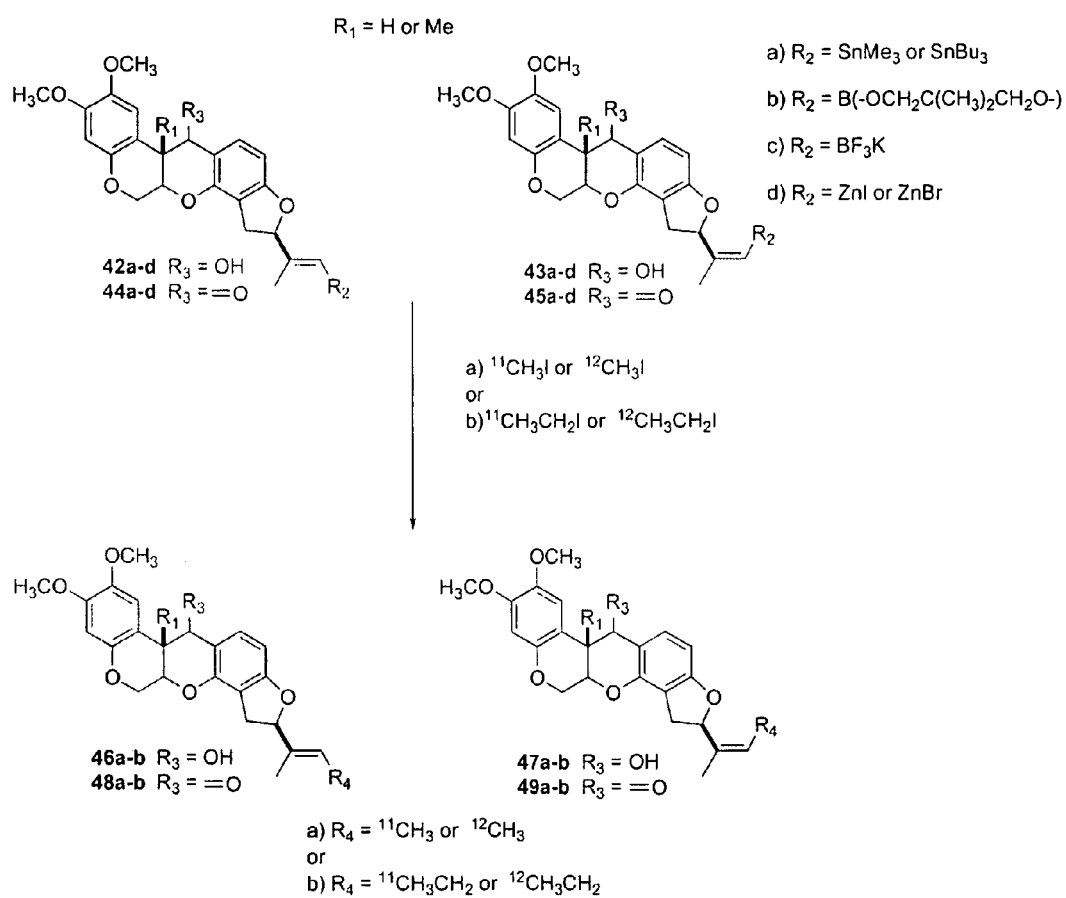
FIG. 12 shows a synthetic pathway in accordance with one embodiment of the present invention for the synthesis of carbon-labeled rotenone analogs.
Figure 13:
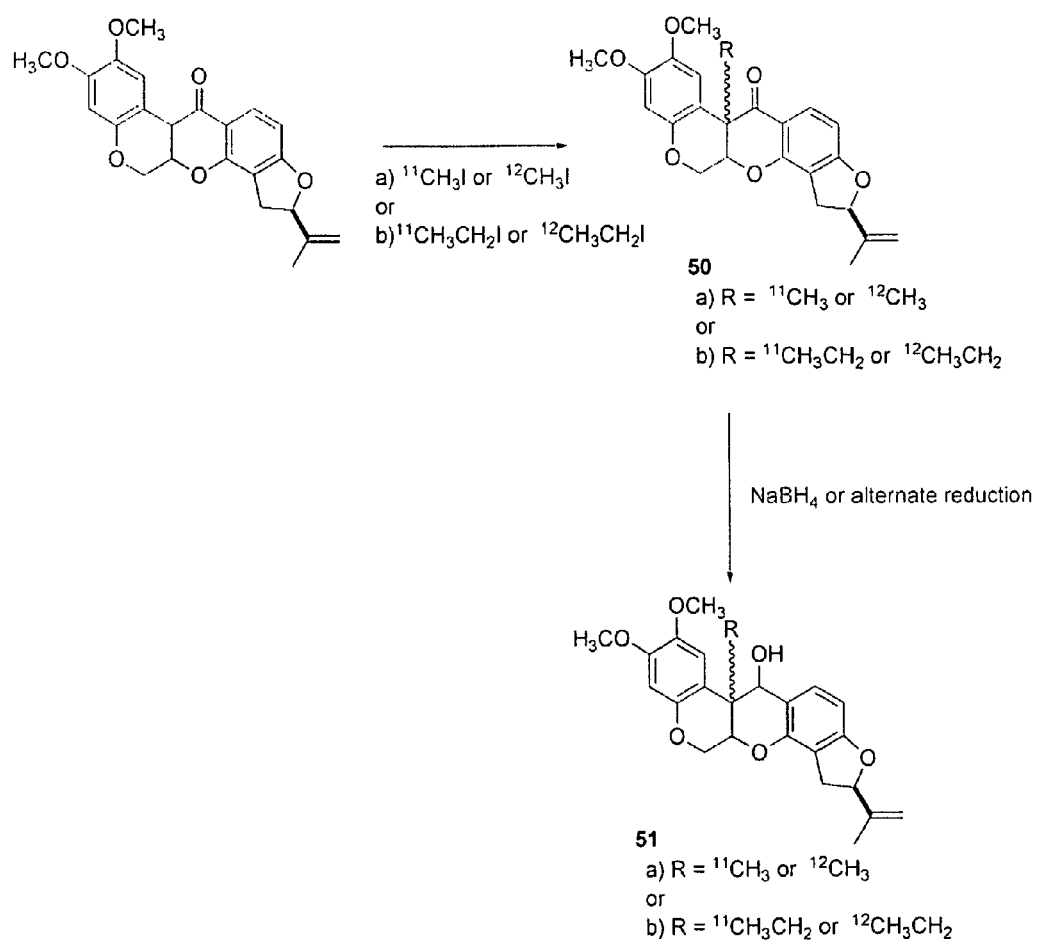
FIG. 13 shows a synthetic pathway in accordance with one embodiment of the present invention for the synthesis of carbon-labeled rotenone analogs.
Figure 14:
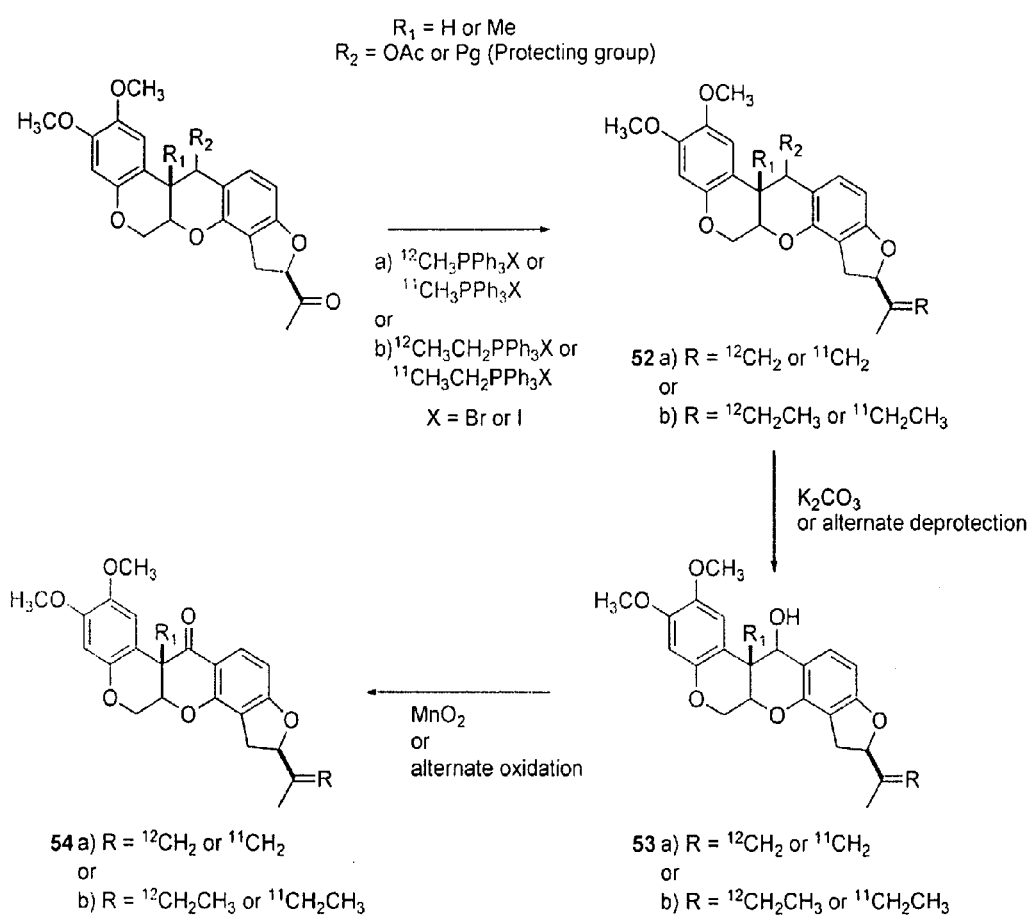
FIG. 14 shows a synthetic pathway in accordance with one embodiment of the present invention for the synthesis of carbon-labeled rotenone analogs.

Evaluation of the iodorotenol and iodorotenone compounds. Z-7'-iodorotenol, E-7'-iodorotenol, Z-7'-iodorotenone, and E-7'-iodorotenone compounds were evaluated in 200+g male Sprague-Dawley rats. Twenty microcuries of the compound was injected into the rat tail vein. At various time points post injection (30 m, 1 h, 2 h, and 4 h) rats were euthanized and the organs and blood were weighed and counted. The results are shown in FIG. 5 and FIG. 6. The E-iodorotenol uptake in the heart was substantially higher than expected with a two-fold increase over the Z isomer. Similarly, the E-iodorotenone demonstrated nearly double the heart uptake as the Z-iodorotenone with 6.5% injected dose in the heart tissue at 1 hour.

The most significant finding was the huge increase in heart-to-blood ratio for the E isomer (FIG. 6). With a 1 hour value of 140:1 and a 2 hour value exceeding 160:1 indicating that the E isomer has high extraction properties in the heart tissue. The absolute heart uptake and the heart-to-blood ratios for the E compounds relative to the Z compounds were not expected and could not be predicted from this small structural change.

Figure 17:
FIG. 17 shows planar images in canine injected with Z-iodorotenone or E-iodorotenone.
Figure 17:
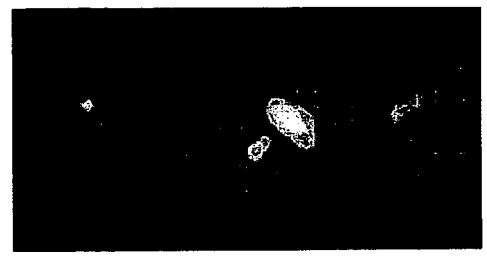
Figure 17:
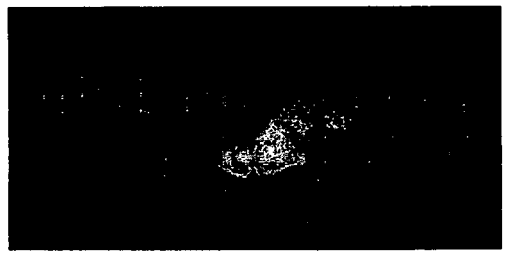
Figure 17:

Z-7'-iodorotenone and E-7'-iodorotenone compounds were also evaluated in canines. Two 20-25 kg dogs were anesthetized with iv sodium pentathol and maintained on inhaled isoflurane. Four to six mCi of Z-[$^{123}$I]Iodorotenone or E-[$^{123}$I]Iodorotenone was injected in a front leg vein. Dual head planar imaging was carried out using the GE Millenium SPECT scanner with Hawkeye xray CT. The scanning protocol was serial 4 m whole body scans over the first hour, 8 m whole body scans from 1-2 h and 30 min whole body scans out to 7 h post injection of the tracer. The planar images are shown in FIG. 17. The E-iodorotenone showed greater heart uptake and retention. The heart is clearly visable out to 4.5 hours. The Z-iodorotenone washed out of the heart faster and cleared through the gallbaldder and stomach more rapidly. No thyroid blocking agent was introduced prior to the scan. The bright spot in the throat region in the Z-iodorotenone scan is salivary gland. The uptake of both compounds in the thyroid was minimal.

Figure 15:
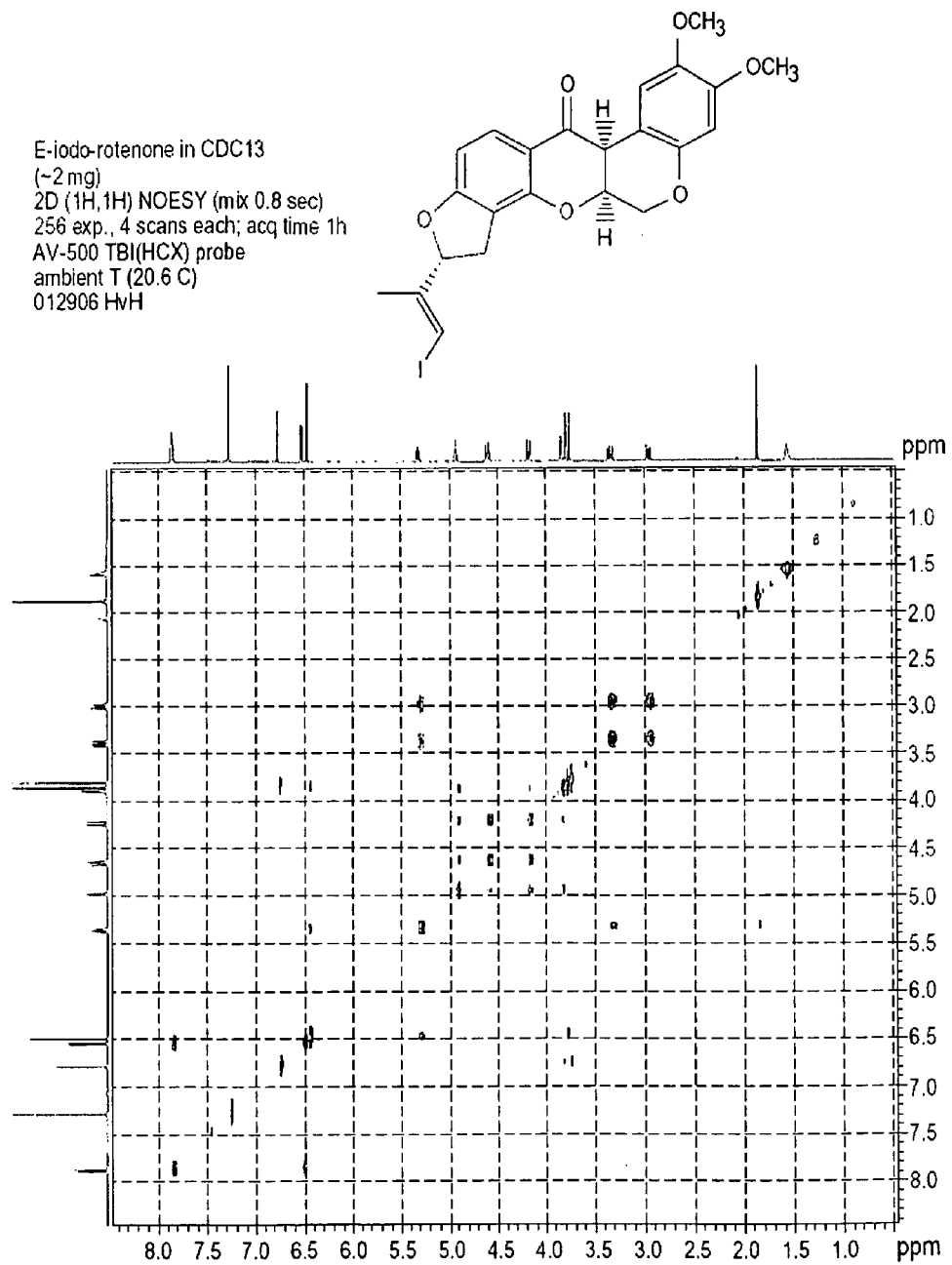
FIG. 15 shows the NMR NOESY spectra confirming the configuration of E-iodorotenone.
Figure 16:
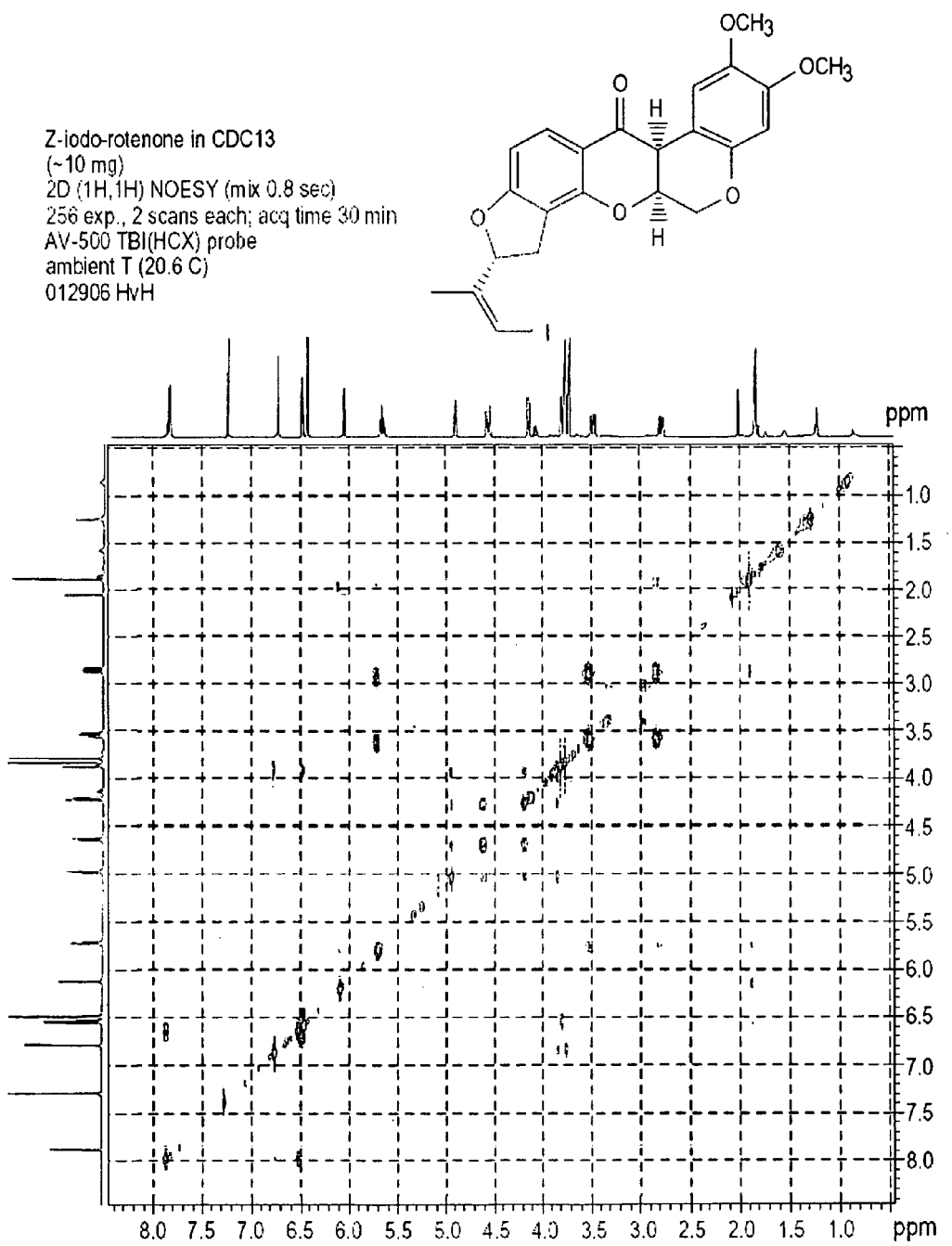
FIG. 16 shows the NMR NOESY spectra confirming the configuration of Z-iodorotenone.

NMR spectra of the E-iodorotenone and Z-iodorotenone are shown in FIG. 15 and FIG. 16. These NOESY spectra show the through space interactions of the protons on the molecule. From this one may determine the structure of the molecule. These spectra confimed the configuration of E- and Z-iodorotenone.

12-Rotenol Synthesis: Rotenone (2 g, 5 mmol) was suspended in methanol (50 mL) and was cooled to 0° C. in an ice bath. Added solid NaBH$_4$ (770 mg, 20 mmol) in one portion and the mixture was stirred for 1 h at 0° C. The reaction mixture was allowed to come to room temperature. Water (100 mL) was added, extracted with dichloromethane (3×50 mL), washed with brine, dried over anhydrous Na$_2$SO$_4$, filtered, and evaporated to obtain a fluffy solid, which was purified by flash column chromatography on silica gel using EtOAc:Hexane (1:3) to afford rotenol as colorless fluffy solid (1.98 g, 98%). m. p.: 80-82° C.; $^1$H NMR (CDCl$_3$): δ 7.03 (d, 1H, J=7.96 Hz, 11-H); 6.68 (s, 1H, 1-H); 6.45 (s, 1H, 4-H), 6.44 (d, 1H, J=7.96 Hz, 10-H); 5.19 (t, 1H, J=8.89 Hz, 5'H); 5.07 (s, 1H, 7'H); 4.90 (br s, 2H, 7'-H and 12-H); 4.8-4.9 (ddd, 1H, J=5.14, 5.28, 10.68 Hz, 6a-H); 4.60 (dd, 1H, J=10.08, 10.68 Hz, 6'-Hβ); 4.22 (dd, 1H, J=5.14, 10.08 Hz, 6'-Hα); 3.84 (s, 3H, 3-OCH$_3$); 3.83 (s, 3H, 2-OCH$_3$); 3.37 (dd, 1H, J=4.97, 5.28 Hz, 12a-H); 3.28 (dd, 1H, J=8.89, 15.67 Hz, 4'-Hβ); 2.94 (dd, 1H, J=8.89, 15.67 Hz, 4'-Hα); 1.79 (s, 3H, 8'-CH$_3$); $^{13}$C NMR (CDCl$_3$): δ 188.73 (C-12); 167.14 (C-9); 157.73 (C-7a); 149.23 (C-3); 147.19 (C-4a); 143.61 (C-2); 142.83 (C-6'); 129.77 (C-11); 113.14 (C-11a); 112.80 (C-8); 112.40 (C-7'); 110.09 (C-1); 104.68 (C-10); 104.63 (C-12b); 100.70 (C-4); 87.66 (C-5'); 72.04 (C-6a); 66.10 (C-6); 56.13 (OCH$_3$); 55.69 (OCH$_3$); 44.41 (C-12a); 31.12 (C-4'); 17.00 (C-8').

Rotenol Acetate Synthesis: Rotenol (1.58 g, 4.0 mmol) was dissolved in dry CH$_2$Cl$_2$ (20 mL) and cooled to 0° C. under argon atmosphere. Added dimethylaminopyridine (DMAP, 586 mg, 4.8 mmol) followed by acetic anhydride (449 mg, 0.415 mL, 4.4 mmol) and the mixture was stirred for 1 hour. Added a few drops of methanol and the solvent was evaporated. The crude residue was purified by flash column chromatography on silica gel using EtOAc:Hexane (1:5) to afford the acetate as white crystalline solid (1.72 g, 98%); m. p.: 107-109° C.; $^1$H NMR (300 MHz, CDCl$_3$): δ 7.05 (d, 1H, J=7.96 Hz, 11-H); 6.65 (s, 1H, 1-H); 6.43 (s, 1H, 4-H), 6.42 (d, 1H, J=7.96 Hz, 10-H); 6.15 (d, J=3.76 Hz, 1H, 12-H); 5.16 (t, 1H, J=8.89 Hz, 5'H); 5.07 (s, 1H, 7'H); 4.90 (br s, 1H, 7'-H); 4.81-4.90 (ddd, 1H, J=5.14, 5.28, 10.68 Hz, 6a-H); 4.62 (dd, 1H, J=10.08, 10.68 Hz, 6-Hβ); 4.21 (dd, 1H, J=5.14, 10.08 Hz, 6-Hα); 3.82 (s, 6H, 3-OCH$_3$, 2-OCH$_3$); 3.47 (dd, 1H, J=4.97, 5.28 Hz, 12a-H); 3.28 (dd, 1H, J=8.89, 15.67 Hz, 4'-Hβ); 2.98 (dd, 1H, J=8.89, 15.67 Hz, 4'-Hα); 1.81 (s, 3H, OAc); 1.79 (s, 3H, 8'-CH$_3$); $^{13}$C NMR (100 MHz, CDCl$_3$): δ 169.87 (C=O of OAc); 162.11 (C-9); 149.70 (C-7a); 149.31 (C-3); 148.55 (C-4a); 143.72 (C-2); 143.41 (C-6'); 131.03 (C-11); 112.71 (C-11a); 111.98 (C-8); 111.81 (C-7'); 111.05 (C-1); 108.66 (C-10); 102.88 (C-12b); 100.07 (C-4); 86.61 (C-5'); 68.97 (C-6a); 66.61 (C-12); 64.48 (C-6); 56.33 (OCH$_3$); 55.76 (OCH$_3$); 36.45 (C-12a); 31.88 (C-4'); 20.78 (COCH$_3$); 17.16 (C-8'); MS (m/z, %): 438 (55); 379 (M-59, 76); 307 (15); 192 (100); HRMS Calcd. For C$_{25}$H$_{26}$O$_7$, 438.1679; Found, 438.1687.

Rotenol Ketoacetate Synthesis: To a solution of the acetate (6.58 g, 15 mmol) in a mixture of dry THF (75 mL) and water (75 mL) was added a small crystal of OsO$_4$ (~5 mg) and one drop of pyridine (~25 µL). After stirring for 2-3 minutes added NaIO$_4$ (9.6 g, 45 mmol) in one portion and the reaction mixture was stirred for 2 h by allowing to come to room temperature. Added more water (100 mL), extracted with CH$_2$Cl$_2$ (3×200 mL) washed successively with sodium metabisulfite (100 mL) and brine (100 mL), dried over anhydrous Na$_2$SO$_4$, filtered, and evaporated. The crude residue was purified by flash column chromatography on silica gel using EtOAc:hexane (3:7) to afford the ketoacetate as colourless solid (5.2 g, 78%); m. p.: 132-134° C.; $^1$H NMR (CDCl$_3$): δ 7.08 (d, J=8.20 Hz, 1H, 11-H); 6.71 (s, 1H, 1-H); 6.66 (d, J=8.20 Hz, 1H, 10-H); 6.42 (s, 1H, 4-H); 6.25 (d, J=3.75 Hz, 1H, 12-H); 5.08 (dd, J=6.68, 10.84 Hz, 1H, 5'-H); 4.82 (ddd, J=5.10, 5.18, 11.07 Hz, 1H, 6a-H); 4.44 (dd, J=9.84, 11.07 Hz, 1H, 6-Hβ); 4.22 (dd, J=5.18, 9.84 Hz, 1H, 6-Hα); 3.85 (s, 6H, 3-OCH$_3$, 2-OCH$_3$); 3.52 (dd, J=6.68, 16.08 Hz, 1H, 12a-H); 3.42 (dd, J=4.63, 5.10 Hz, 1H, 4'-Hβ); 3.24 (dd, J=10.84, 16.08 Hz, 1H, 4'-Hα); 2.28 (s, 3H, 8'-CH$_3$); 1.76 (s, 3H, OAc); $^{13}$C NMR (100 MHz, CDCl$_3$): δ 208.25, 160.23, 150.46, 149.42, 149.26, 144.68, 126.98, 123.83, 117.61, 111.57, 111.55, 110.51, 105.07, 103.09, 100.93, 86.49, 71.09, 70.88, 67.79, 56.35, 55.97, 29.89, 26.24; MS (m/z, %): 438 (42); 379 (M-59, 55); 192 (100).

Rotenone Z-Iodoacetate Synthesis: Wittig salt (7.22 g, 13.6 mmol) was suspended in dry THF (60 mL) and cooled to 0° C. in an ice bath under argon atmosphere. A solution (TMS)$_2$NNa in THF (1M, 13.6 mL, 13.6 mmol) was added dropwise and the mixture was stirred for 15 minutes at 0° C. The suspension dissolved to a yellow-orange solution. The solution was cooled to −78° C. and a solution of ketoacetate (5.0 g, 11.4 mmol) in THF was added dropwise. The reaction mixture was stirred at −78° C. for 4 hours and then allowed to come to room temperature. Added water (100 mL) and extracted with dichloromethane (3×100 mL). The organic extracts were collected, washed with brine, and evaporated to get a brown syrup, which was purified by flash column chromatography on silica gel using EtOAc:hexane (1:4) to afford the Z-iodoacetate as colorless solid (5.27 g, 82%); m.p.: 132-134° C.; $^1$H NMR (CDCl$_3$): δ 7.07 (d, J=7.96 Hz, 1H, 11-H); 6.65 (s, 1H, 1-H); 6.42 (d, J=7.96 Hz, 1H, 10-H); 6.40 (s, 1H, 4-H); 6.26 (d, J=4.42 Hz, 1H, 12-H), 6.05 (s, 1H, 7'-H); 5.63 (dd, J=6.68, 9.28 Hz, 5'-H); 4.94 (ddd, J=5.75, 5.97, 11.28 Hz, 1H, 6a-H); 4.43 (dd, J=10.18, 21.23 Hz, 1H, 6'-Hβ); 4.23 (dd, J=4.86, 9.73 Hz, 1H, 6'-Hα); 3.82 (s, 6H, 2×OCH$_3$); 3.28 (dd, J=6.68, 16.36 Hz, 1H, 12a-H); 3.22 (dd, J=6.20, 9.73 Hz, 1H, 4'-Hβ); 2.82 (dd, J=8.18, 16.36 Hz, 1H, 4'-Hα); 1.92 (s, 3H, 8'-CH$_3$); 1.78 (s, OAc); $^{13}$C NMR (CDCl$_3$): δ 170.07, 162.22, 149.82, 149.39, 148.59, 146.63, 143.49, 131.18, 112.69, 111.72, 111.32, 108.55, 103.04, 100.14, 87.48, 74.92, 69.07, 66.63, 64.57, 56.44, 55.89, 36.54, 31.59, 20.92, 18.84; MS (m/z, %): 564 (40); 505 (M-59, 51); 307 (15); 192 (100); HRMS Calcd. For C$_{25}$H$_{25}$O$_7$I, 564.0645; Found, 564.0657.

Bromoacetate Synthesis Wittig salt (1.09 g, 2.5 mmol) was suspended in dry THF (10 mL) and cooled to 0° C. in an ice bath under argon atmosphere. A solution of (TMS)$_2$NNa (1 M solution in THF, 2.2 mL, 2.2 mmol) was added dropwise and the mixture was stirred for 15 minutes at 0° C. The suspension was dissolved to a yellow-orange solution. The solution was cooled to −78° C. and a solution of ketoacetate (880 mg, 2 mmol) was added dropwise. The reaction mixture was stirred at −78° C. for 4 hours and then allowed to come to room temperature. Added water (50 mL) and extracted with dichloromethane (3×50 mL). The organic extracts were collected, washed with brine, and evaporated to get a brown syrup, which was purified by flash column chromatography on silica gel using EtOAc:hexane (1:4) to afford the bromoacetate (Z/E ratio=approximately, 11:9) as colorless solid (827 mg, 80%); m. p. 124-127° C.; $^1$H NMR (CDCl$_3$): δ 7.05 (d, J=7.98 Hz, 1H, 11-H); 6.62 (s, 1H, 1-H); 6.42 (d, J=7.98 Hz, 1H, 10-H); 6.40 (s, 1H, 4-H); 6.26 (d, J=4.40 Hz, 1H, 12-H), 6.39, 6.01 (2s, 1H, 7'-H, mixture of E/Z isomers); 5.83, 5.23 (2dd, J=6.68, 9.42 Hz, 5'-H, mixture of E/Z isomers); 4.96 (ddd, J=5.74, 5.98, 11.26 Hz, 1H, 6a-H); 4.43 (m, 1H, 6'-Hβ); 4.23 (m, 1H, 6'-Hα); 3.83 (s, 6H, 2×OCH$_3$); 3.28 (m, 1H, 12a-H); 3.22, 3.18 (2dd, J=6.22, 9.78 Hz, 1H, 4'-Hβ); 2.98, 2.84 (2dd, J=8.20, 16.38 Hz, 1H, 4'-Hα); 1.90 (2s, 3H, 8'-CH$_3$); 1.78 (s, OAc); $^{13}$C NMR (100 MHz, CDCl$_3$): δ 170.00 (C=O of OAc); 162.11 (C-9); 161.68 (C-7a); 149.87, 149.78 (C-3); 149.35 (C-4a); 148.56 (C-12); 143.45 (C-2); 141.19, 140.18 (C-6'); 131.21 (C-11); 112.70 (C-10); 112.20, 111.71 (C-8); 111.49, 111.28 (C-7'); 108.54 (C-1); 105.73 (C-10); 102.98, 101.95 (C-12b); 100.11 (C-4); 86.1, 83.16 (C-5'); 69.01, 66.59 (C-6a); 64.53 (C-6); 56.40 (OCH$_3$); 55.86 (OCH$_3$); 36.47 (C-12a); 31.80, 31.59 (C-4'); 20.88 (COCH$_3$) 17.08, 14.89 (C-8'); MS (m/z, %): 518 (78); 516 (75); 459 (85); 457 (90); 307 (15); 289 (10); 192 (100); HRMS Calcd for C$_{25}$H$_{25}$O$_7$I, 516.0784; Found, 516.0792.

Z-Iodorotenol Synthesis: Z-Iodoacetate (5.0 g, 8.87 mmol) was dissolved in minimum amount of CH$_2$Cl$_2$ (10 mL) and added to a 1:1 mixture of MeOH:H$_2$O (32 mL) followed by solid potassium carbonate (3.7 mg, 27 mmol). The mixture was heated at 60° C. for 4 hours with vigorous stirring. The mixture was cooled to room temperature, water was added (100 mL), and extracted with CH$_2$Cl$_2$ (3×100 mL). The organic extracts were collected, washed with brine, dried over anhydrous Na$_2$SO$_4$, filtered, and evaporated to get a syrup, which was purified by flash column chromatography on silica gel using EtOAc:hexane (2:3) to afford the Z-iodoalcohol as a white solid (4.25 g, 92%); m.p.: 80-82° C.; $^1$H NMR (CDCl$_3$): δ 7.07 (d, 1H, J=8.15 Hz, 11-H); 6.71 (s, 1H, 1-H); 6.48 (s, 1H, 4-H), 6.46 (d, 1H, J=8.15 Hz, 10-H); 6.05 (d, J=1.42 Hz, 1H, 7'-H); 5.67 (dd, J=8.46, 9.66 Hz, 1H, 5'-H); 4.93 (d, J=4.26 Hz, 1H, 12-H); 4.84 (ddd, J=4.98, 5.13, 11.34 Hz, 1H, 6a-H); 4.61 (dd, J=9.76, 11.34 Hz, 1H, 6'-Hβ); 4.24 (dd, J=5.13, 9.76 Hz, 1H, 6'-Hβ); 3.86 (s, 3H, 3-OCH$_3$); 3.85 (s, 3H, 2-OCH$_3$); 3.48 (dd, J=8.46, 15.98 Hz, 1H, 4'-Hβ); 3.40 (dd, J=4.26, 4.98 Hz, 1H, 12a-H); 2.83 (dd, J=9.66, 15.98 Hz, 1H, 4'-Hα); 1.89 (d, J=1.42 Hz, 3H, 8'-CH$_3$); $^{13}$C NMR (CDCl$_3$): δ 161.84, 149.61, 149.33, 149.24, 146.75, 143.77, 130.56, 114.19, 112.66, 111.46, 108.82, 102.75, 100.68, 87.35, 74.88, 69.29, 66.28, 65.04, 56.59, 55.87, 38.08, 31.67, 18.86, 14.24; MS (m/z, %): 522 (M$^+$, 26); 505 (32); 307 (8); 192 (100); HRMS Calcd. For C$_{23}$H$_{23}$O$_6$I, 522.0539; Found, 522.0546.

E/Z-Bromorotenol Synthesis: E/Z-Bromoacetate (476 mg, 0.92 mmol) was dissolved in minimum amount of CH$_2$Cl$_2$ (1 mL) and added to a 1:1 mixture of MeOH:H$_2$O (10 mL) followed by solid potassium carbonate (635 mg, 4.6 mmol). The mixture was heated at 60° C. for 4 h with vigorous stirring. The mixture was cooled to room temperature, water was added (25 mL), and extracted with CH$_2$Cl$_2$ (3×25 mL). The organic extracts were collected, washed with brine, dried over anhydrous Na$_2$SO$_4$, filtered, and evaporated to get a syrup, which was purified by flash column chromatography on silica gel using EtOAc:hexane (2:3) to afford the bromoalcohol as a white solid (420 mg, 96%). The E/Z mixture of bromorotenol was separated by HPLC; m. p.: 122-124° C.; $^1$H NMR (CDCl$_3$): δ 7.02 (d, J=8.12 Hz, 1H, 11-H); 6.70 (s, 1H, 1-H); 6.43 (s, 1H, 4-H); 6.41 (d, J=8.12 Hz, 1H, 10-H); 6.40, 6.01 (2s, 1H, 7'-H); 5.82, 5.23 (2dd, J=8.45, 9.75 Hz, 1H, 5'-H); 4.95 (bs, 1H, 12-H); 4.81 (ddd, J=5.10, 5.13, 11.45 Hz, 1H, 6a-H); 4.60 (dd, J=9.76, 11.45 Hz, 1H, 6'-Hβ); 4.22 (dd, J=5.42, 9.76 Hz, 1H, 6'-Hα); 3.81 (s, 3H, OCH$_3$); 3.80 (s, 3H, OCH$_3$); 3.44, 3.24 (2dd, J=9.66, 15.98 Hz, 1H, 4'-Hβ); 3.40 (dd, J=4.35, 5.25 Hz, 1H, 12a-H); 2.99, 2.82 (2dd, J=8.55, 15.98 Hz, 1H, 4'-Hα); 1.91, 1.90 (2s, 3H, 8'-CH$_3$); $^{13}$C NMR (CDCl$_3$): δ 161.84, 161.39, 149.68, 149.34, 149.21, 143.84, 141.29, 140.30, 130.64, 130.58, 114.25, 114.06, 112.75, 112.23, 111.38, 108.73, 105.63, 102.76, 102.72, 101.89, 100.72, 86.05, 83.09, 69.25, 66.27, 65.02, 60.43, 56.58, 55.88, 38.09, 31.88, 31.66, 17.11, 14.96, 14.22; MS (m/z, %).

Z-Bromorotenol: m. p. 120-122° C.; $^1$H NMR (CDCl$_3$): δ 7.03 (d, J=8.12 Hz, 1H, 11-H); 6.70 (s, 1H, 1-H); 6.43 (s, 1H, 4-H); 6.41 (d, J=8.12 Hz, 1H, 10-H); 6.01 (s, 1H, 7'-H); 5.82 (dd, J=8.45, 9.75 Hz, 1H, 5'-H); 4.96 (bs, 1H, 12-H); 4.81 (ddd, J=5.10, 5.13, 11.45 Hz, 1H, 6a-H); 4.60 (dd, J=9.76, 11.45 Hz, 1H, 6'-Hβ); 4.22 (dd, J=5.42, 9.76 Hz, 1H, 6'-Hα); 3.81 (s, 3H, OCH$_3$); 3.80 (s, 3H, OCH$_3$); 3.44 (dd, J=9.66, 15.98 Hz, 1H, 4'-Hβ); 3.40 (dd, J=4.35, 5.25 Hz, 1H, 12a-H); 2.82 (dd, J=8.55, 15.98 Hz, 1H, 4'-Hα); 1.91, (s, 3H, 8'-CH$_3$). $^{13}$C NMR (CDCl$_3$).

E-Bromorotenol: m. p. 124-126° C.; $^1$H NMR (CDCl$_3$): δ 7.02 (d, J=8.12 Hz, 1H, 11-H); 6.70 (s, 1H, 1-H); 6.43 (s, 1H, 4-H); 6.41 (d, J=8.12 Hz, 1H, 10-H); 6.40 (s, 1H, 7'-H); 5.23 (dd, J=8.45, 9.75 Hz, 1H, 5'-H); 4.97 (bs, 1H, 12-H); 4.81 (ddd, J=5.10, 5.13, 11.45 Hz, 1H, 6a-H); 4.60 (dd, J=9.76, 11.45 Hz, 1H, 6'-Hβ); 4.22 (dd, J=5.42, 9.76 Hz, 1H, 6'-Hα); 3.82 (s, 3H, OCH$_3$); 3.81 (s, 3H, OCH$_3$); 3.40 (dd, J=4.35, 5.25 Hz, 1H, 12a-H); 3.24 (dd, J=9.66, 15.98 Hz, 1H, 4'-Hβ); 2.99 (dd, J=8.55, 15.98 Hz, 1H, 4'-Hα); 1.91, (s, 3H, 8'-CH$_3$); $^{13}$C NMR (CDCl$_3$): δ 161.38, 149.64, 149.29, 143.84, 140.30, 130.64, 114.24, 112.22, 111.36, 108.69, 105.63, 102.71, 100.69, 86.05, 69.28, 66.29, 65.01, 56.57, 55.87, 38.07, 31.88, 14.96.

Z-Iodorotenone Synthesis: To a solution of Z-iodorotenol (250 mg, 0.478 mmol) in dry acetonitrile (5 mL) was added activated manganese dioxide (625 mg, 7.18 mmol) at once under argon atmosphere and the mixture was stirred vigorously at room temperature for 1 minute. The mixture was filtered through a pad of celite, washed several times with dichloromethane, and evaporated to get a residue, which was purified by flash column chromatography on silica gel using EtOAc:hexane (1:3 to 3:7) to furnish Z-iodorotenone as a colourless solid (92 mg, 37%). About 125 mg of Z-iodorotenol was recovered: m. p.: 201-204° C.; $^1$H NMR (300 MHz, CDCl$_3$): δ 7.83 (d, J=8.56 Hz, 1H, 11-H); 6.74 (s, 1H, 1-H); 6.50 (d, J=8.56 Hz, 1H, 10-H); 6.45 (s, 1H, 4-H); 6.07 (s, 1H, 7'-H); 5.68 (dd, J=8.88, 9.63 Hz, 1H, 5'-H); 4.93 (m, 1H, 6a-H); 4.60 (dd, J=3.24, 12.03 Hz, 1H, 6-Hβ); 4.17 (d, J=12.03 Hz, 1H, 6-Hα); 3.84 (d, J=4.26 Hz, 1H, 12a-H); 3.80 (s, 3H, 3-OCH$_3$); 3.76 (s, 3H, 2-OCH$_3$); 3.50 (dd, J=8.88, 16.01 Hz, 1H, 4'-Hβ); 2.81 (dd, J=9.63 Hz, 16.01 Hz, 1H, 4'-Hα); 1.87 (s, 3H, 8'-CH$_3$); $^{13}$C NMR (100 MHz, CDCl$_3$): δ 188.96, 167.38, 157.85, 149.54, 147.38, 145.87, 143.91, 130.10, 113.47, 112.92, 110.32, 104.96, 104.68, 100.94, 88.66, 75.49, 72.26, 71.03, 66.24, 56.34, 55.87, 44.62, 31.00, 18.81; MS (m/z, %): 521 (M+1, 48); 520 (52); 307 (26); 289 (15); 192 (55); 154 (100); HRMS Calcd. For C$_{23}$H$_{21}$IO$_6$, 520.0383; Found, 520.0378; Elemental Analysis: Calcd for C$_{23}$H$_{24}$O$_6$: C, 68.91; H, 5.99; Found: C, 69.06; H, 6.12.

E/Z-Bromorotenone Synthesis: To a solution of E/Z-bromorotenol (100 mg, 0.21 mmol) in dry acetonitrile (5 mL) was added activated manganese dioxide (275 mg, 3.2 mmol) at once under argon atmosphere and the mixture was stirred vigorously at room temperature for 1 minute. The mixture was filtered through a pad of celite, washed several times with dichloromethane, and evaporated to get a residue, which was purified by flash column chromatography on silica gel using EtOAc:hexane (1:3 to 3:7) bromorotenone as a colourless solid (40 mg, 40%). m. p. 192-194° C.; $^1$H NMR (CDCl$_3$): δ 7.85 (d, J=8.63 Hz, 1H, 11-H); 6.76 (s, 1H, 1-H); 6.51 (d, J=8.62 Hz, 1H, 10-H); 6.46 (s, 1H, 4-H); 6.39, 6.04 (2s, 1H, 7'-H, E/Z isomers); 5.85, 5.28 (dd, J=9.06, 9.28 Hz, 1H, 5'-H); 4.94 (dd, J=2.88, 3.09 Hz, 1H, 6a-H); 4.61 (dd, J=2.65, 9.29 Hz, 1H, 6-Hβ); 4.12 (d, J=12.38 Hz, 1H, 6-Hα); 3.86 (d, J=3.76 Hz, 1H, 12a-H); 3.81 (s, 3H, 3-OCH$_3$); 3.77 (s, 3H, 2-OCH$_3$); 3.51, 3.35 (2dd, J=9.95, 15.92 Hz, 1H, 4'-Hβ); 2.97, 2.86 (2dd, J=8.40, 16.01 Hz, 1H, 4'-Hα); 1.81, 1.80 (2d, J=0.66, 1.32, 3H, 8'-CH$_3$); $^{13}$C NMR (CDCl$_3$): δ 188.99, 167.32, 157.85, 149.38, 147.50, 143.89, 140.44, 139.51, 130.18, 130.09, 113.54, 113.46, 112.94, 112.63, 110.29, 106.82, 104.93, 104.67, 102.51, 100.91, 87.23, 84.39, 72.26, 70.91, 66.24, 56.33, 55.87, 44.61, 31.20, 31.01, 17.07, 14.85.

Z-Bromorotenone: $^1$H NMR (CDCl$_3$): δ 7.85 (d, J=8.63 Hz, 1H, 11-H); 6.76 (s, 1H, 1-H); 6.50 (d, J=8.62 Hz, 1H, 10-H); 6.45 (s, 1H, 4-H); 6.04 (s, 1H, 7'-H); 5.85 (dd, J=9.06, 9.28 Hz, 1H, 5'-H); 4.94 (dd, J=2.86, 3.01 Hz, 1H, 6a-H); 4.60 (dd, J=2.65, 9.29 Hz, 1H, 6-Hβ); 4.12 (d, J=12.38 Hz, 1H, 6-Hα); 3.86 (d, J=3.76 Hz, 1H, 12a-H); 3.81 (s, 3H, 3-OCH$_3$); 3.77 (s, 3H, 2-OCH$_3$); 3.51 (dd, J=9.95, 16.01 Hz, 1H, 4'-Hβ); 2.86 (dd, J=8.40 Hz, 16.01 Hz, 1H, 4'-Hα); 1.80 (d, J=1.32 Hz, 3H, 8'-CH$_3$); $^{13}$C NMR (100 MHz, CDCl$_3$): δ 188.97, 167.38, 157.85, 147.37, 145.87, 143.89, 130.10, 113.47, 112.92, 110.29, 104.97, 104.67, 100.93, 88.66, 75.49, 72.26, 66.24, 56.34, 55.87, 44.62, 31.00, 18.82.

E-Bromorotenone: $^1$H NMR (CDCl$_3$): δ 7.85 (d, J=8.63 Hz, 1H, 11-H); 6.76 (s, 1H, 1-H); 6.50 (d, J=8.62 Hz, 1H, 10-H); 6.45 (s, 1H, 4-H); 6.39 (s, 1H, 7'-H); 5.28 (dd, J=9.06, 9.28 Hz, 1H, 5'-H); 4.94 (dd, J=2.86, 3.01 Hz, 1H, 6a-H); 4.60 (dd, J=2.65, 9.29 Hz, 1H, 6-Hβ); 4.12 (d, J=12.38 Hz, 1H, 6-Hα); 3.86 (d, J=3.76 Hz, 1H, 12a-H); 3.81 (s, 3H, 3-OCH$_3$); 3.77 (s, 3H, 2-OCH$_3$); 3.35 (dd, J=9.95, 16.01 Hz, 1H, 4'-Hβ); 2.97 (dd, J=8.40 Hz, 16.01 Hz, 1H, 4'-Hα); 1.81 (d, J=1.32 Hz, 3H, 8'-CH$_3$); $^{13}$C NMR (CDCl$_3$): δ 188.98, 167.30, 157.86, 149.38, 147.52, 140.44, 139.51, 130.18, 113.54, 112.23, 106.82, 104.93, 104.67, 102.51, 84.39, 70.91, 66.24, 56.33, 55.88, 44.62, 31.22, 14.85.

Trimethyl Tin Rotenol Acetate Synthesis: Z-Iodorotenol (564 mg, 1 mmol) was dissolved in dry THF (5 mL) under argon. Added hexamethylditin, (393 mg, 1.2 mmol) Pd catalyst (2 mg), and LiCl (51 mg, 1.2 mmol) successively and the mixture was stirred at room temperature for 2 hours. The solvent was evaporated and the crude residue was chromatographed on silica gel using EtOAc:Hexane (1:3) to afford the trimethyl tin compound as white powder (384 mg, 64%). $^1$H NMR (CDCl$_3$): δ 7.06 (d, J=7.96 Hz, 1H, 11-H); 6.72 (s, 1H, 1-H); 6.48 (s, 1H, 4-H); 6.43 (d, J=7.96 Hz, 1H, 10-H); 6.04 (s, 1H, 12-H); 5.75 (s, 1H, 7'-H); 5.22 (t, J=9.51 Hz, 1H, 5'-H); 4.86 (ddd, J=4.73, 5.28, 11.34 Hz, 1H, 6a-H); 4.63 (dd, J=9.78, 11.34 Hz, 1H, 6'-Hβ); 4.26 (dd, J=4.72, 9.78 Hz, 1H, 6'-Hα); 3.87 (s, 3H, 3-OCH$_3$); 3.86 (s, 3H, 2-OCH$_3$); 3.44 (dd, J=4.45, 5.38 Hz, 1H, 12a-H); 3.32 (dd, J=9.34, 15.75 Hz, 1H, 4'-Hβ); 2.92 (dd, J=9.34, 15.75 Hz, 1H, 4'-Hα); 1.91 (d, J=1.22 Hz, 3H, 8'-CH$_3$); 1.84 (s, 3H, OAc); 0.14 (s, 9H, 3×CH$_3$); $^{13}$C NMR (100 MHz, CDCl$_3$): δ 170.00, 162.04, 151.50, 149.76, 149.37, 148.58, 143.49, 131.05, 127.84, 113.09, 111.75, 111.28, 108.63, 103.31, 102.95, 100.12, 88.42, 69.03, 66.72, 64.59, 60.39, 56.42, 55.87, 36.52, 33.04, 21.49, 20.89.

Z-Tributylstannylrotenol Acetate Synthesis: To a solution of Z-iodorotenolacetate (521 mg, 1 mmol) in dry THF (20 mL) was added hexabutylditin (870 mg, 1.5 mmol), allylpalladium dimer (10 mg), and lithium chloride (60 mg, 1.5 mmol) under argon. The mixture was stirred under argon for 4 hours at room temperature and passed through a short silica gel column eluting with CH$_2$Cl$_2$. Concentration under reduced pressure afforded a residue, which was purified by flash column chromatography on silica gel using EtOAc: hexane (1:4) to yield Z=tributylstannylrotenolacetate as colorless oil (414 mg, 62%); $^1$H NMR (CDCl$_3$): δ 7.05 (d, J=8.10 Hz, 1H, 11-H); 6.71 (s, 1H, 1-H); 6.47 (s, 1H, 4-H); 6.42 (d, J=8.10 Hz, 1H, 10-H); 6.05 (s, 3H, 12-H); 5.73 (d, J=1.22 Hz, 1H, 7'-H); 5.12 (t, J=9.34 Hz, 1H, 5'-H); 4.83 (ddd, J=4.72, 5.28, 11.34 Hz, 1H, 6a-H); 4.62 (dd, J=9.78, 11.34 Hz, 1H, 6'-Hβ); 4.24 (dd, J=4.72, 9.78 Hz, 1H, 6'-Hα); 3.85 (s, 3H, 3-OCH$_3$); 3.84 (s, 3H, 2-OCH$_3$); 3.39 (dd, J=4.29, 5.28 Hz, 1H, 12a-H); 3.25 (dd, J=9.34, 15.75 Hz, 1H, 4'-Hβ); 2.95 (dd, J=9.34, 15.75 Hz, 1H, 4'-Hα); 1.89 (d, J=1.22 Hz, 3H, 8'-CH$_3$); 1.82 (s, 3H, OA c); 1.44-1.50 (m, 6H, 3×CH$_2$); 1.26-1.36 (m, 6H, 3×CH$_2$); 0.85-0.93 (m, 15H, 3×CH$_2$CH$_3$).

Z-Tributylstannylrotenol Synthesis: Z-Tributyltinrotenol acetate (364 mg, 0.5 mmol) was dissolved in minimum amount of $CH_2Cl_2$ (1 mL) and added to a 1:1 mixture of methanol:water (10 mL). Added solid potassium carbonate (345 mg, 2.5 mmol) and the mixture was stirred vigorously overnight at room temperature. Added more water (25 mL) and extracted with dichloromethane (3×25 mL). Washed with brine and dried over sodium sulfate, filtered and evaporated to get a residue, which was purified by flash column chromatography on silica gel using EtOAc:Hexane (1:4) to obtain the tributyltin rotenol (335 mg, 98%) as white glassy solid. $^1$H NMR ($CDCl_3$): δ 7.04 (d, J=8.10 Hz, 1H, 11-H); 6.70 (s, 1H, 1-H); 6.46 (s, 1H, 4-H); 6.43 (d, J=8.10 Hz, 1H, 10-H); 5.73 (d, J=1.22 Hz, 1H, 7'-H); 5.12 (t, J=9.34 Hz, 1H, 5'-H); 4.92 (br s, 1H, 12-H); 4.83 (ddd, J=4.72, 5.28, 11.34 Hz, 1H, 6a-H); 4.62 (dd, J=9.78, 11.34 Hz, 1H, 6-Hβ); 4.24 (dd, J=4.72, 9.78 Hz, 1H, 6-Hα); 3.85 (s, 3H, 3-$OCH_3$); 3.84 (s, 3H, 2-$OCH_3$); 3.39 (dd, J=4.29, 5.28 Hz, 1H, 12a-H); 3.25 (dd, J=9.34, 15.75 Hz, 1H, 4'-Hβ); 2.95 (dd, J=9.34, 15.75 Hz, 1H, 4'-Hα); 1.89 (d, J=1.22 Hz, 3H, 8'-$CH_3$); 1.44-1.50 (m, 6H, 3×$CH_2$); 1.26-1.36 (m, 6H, 3×$CH_2$); 0.85-0.93 (m, 15H, 3×$CH_2CH_3$); $^{13}$C NMR (100 MHz, $CDCl_3$): d 162.03, 151.83, 149.37, 149.13, 143.89, 130.45, 127.39, 113.23, 111.32, 108.79, 103.02, 100.75, 89.02, 70.97, 69.19, 66.34, 65.05, 56.57, 55.89, 38.14, 32.69, 29.15, 20.87, 17.53, 13.72, 13.63, 10.67; MS ($M^+$, %): 685 (45); 669 (22); 629 (100); 379 (18); 192 (52); 179 (74); HRMS Calcd for $C_{35}H_{50}O_6Sn$, 686.2601, Found, 686.2605.

E-tributyl Tin Rotenol: $^1$H NMR ($CDCl_3$): δ 7.04 (d, J=8.10 Hz, 1H, 11-H); 6.75 (s, 1H, 1-H); 6.45 (s, 1H, 4-H); 6.43 (d, J=8.10 Hz, 1H, 10-H); 5.97 (s, 1H, 7'-H); 5.12 (t, J=9.34 Hz, 1H, 5'-H); 4.95 (br s, 1H, 12-H); 4.83 (ddd, J=4.72, 5.28, 11.34 Hz, 1H, 6a-H); 4.62 (dd, J=9.78, 11.34 Hz, 1H, 6-Hβ); 4.24 (dd, J=4.72, 9.78 Hz, 1H, 6-Hα); 3.85 (s, 3H, 3-$OCH_3$); 3.84 (s, 3H, 2-$OCH_3$); 3.39 (dd, J=4.29, 5.28 Hz, 1H, 12a-H); 3.25 (dd, J=9.34, 15.75 Hz, 1H, 4'-Hβ); 2.95 (dd, J=9.34, 15.75 Hz, 1H, 4'-Hα); 1.89 (d, J=1.22 Hz, 3H, 8'-$CH_3$); 1.44-1.50 (m, 6H, 3×$CH_2$); 1.26-1.36 (m, 6H, 3×$CH_2$); 0.85-0.93 (m, 15H, 3×$CH_2CH_3$); MS (m/z, %): 685 (62); 669 (38); 629 (82); 379 (18); 235 (10); 192 (100); HRMS Calcd for $C_{33}H_{30}O_6Sn$, 683.2592; Found, 682.2608.

(Z)-Tributylstannyl Rotenone Synthesis: To a solution of Z-tributystannylrotenol (300 mg, 0.44 mmol) in dry $CH_3CN$ (20 mL) was added $MnO_2$ (730 mg, 8.4 mmol) under argon. The mixture was stirred 5 min at room temperature and then filtered through a pad of celite. Concentration of the filtrate under reduced pressure gave a residue, which was purified by flash column chromatography on silica gel using EtOAc:Hexane (3:7) to yield the Z-tributylstannylrotenone as an oily foam (128 mg, 43%); $^1$H NMR ($CDCl_3$): δ 7.84 (d, J=8.56 Hz, 1H, 11-H); 6.78 (s, 1H, 1-H); 6.49 (d, J=8.56 Hz, 1H, 10-H); 6.46 (s, 1H, 4-H); 5.77 (d, J=1.27 Hz, 1H, 7'-H); 5.16 (t, J=9.33 Hz, 1H, 5'-H); 4.93 (dd, J=3.03, 3.48 Hz, 1H, 6a-H); 4.62 (dd, J=3.03, 12.06 Hz, 1H, 6-Hβ); 4.18 (d, J=12.06 Hz, 1H, 6-Hα); 3.84 (d, J=3.48 Hz, 1H, 12a-H); 3.81 (s, 3H, 3-$OCH_3$); 3.76 (s, 3H, 2-$OCH_3$); 3.29 (dd, J=9.33, 15.88 Hz, 1H, 4'-Hβ); 2.96 (dd, J=9.33, 15.88 Hz, 1H, 4'-Hα); 1.87 (d, J=1.27 Hz, 3H, 8'-$CH_3$); 1.42-1.52 (m, 6H, 3×$CH_2$); 1.22-1.34 (m, 6H, 3×$CH_2$); 0.84-0.91 (m, 15H, 3×$CH_2CH_3$); MS (m/z, %): 683 (24); 627 (M-56, 100); 513 (12); 435 (12); 321 (12); 235 (15); 192 (40); 179 (68); HRMS Calcd for $C_{35}H_{48}O_6Sn$, 684.2562; Found, 684.2560.

12a-Methylrotenone: Rotenone (394 mg, 1 mmol) was dissolved in dry DMF (4 mL) and cooled to 0° C. under argon atmosphere. Sodium hydride (50 mg, 2 mmol) was added with caution and stirred for 15 minutes at 0° C. Added methyl iodide (0.4 mL, excess) and the reaction mixture was heated at 150° C. for 24 h. Cooled to RT, added water (10 mL) and extracted with ether (3×15 mL). The crude product was purified on silica gel column using EtOAc:Hexane (1:3) as eluent to obtain the methylrotenone as colorless oil (115 mg, 28%). $^1$H NMR ($CDCl_3$): δ 7.83 (d, J=8.6 Hz, 1H, 11-H); 7.76 (s, 1H, 1-H); 6.64 (d, J=8.6 Hz, 1H, 10-H); 6.44 (s, 1H, 4-H); 5.39 (dd, 1H, J=9.8, 8.2 Hz, 5'-H); 5.16 (s, 1H, 7'-H); 5.01 (s, 1H, 7'-H); 4.80 (1H, bs, 6a-H); 4.56 (dd, J=11.5, 2.9 Hz, !H, 6H-b); 4.38 (d, J=11.3 Hz, 1H, 6-Ha); 3.80 (s, 3H, $OCH_3$); 3.75 (s, 3H)$CH_3$); 3.30 (dd, J=15.8, 9.8 Hz, 1H, 4'-H); 2.94 (dd, J=15.8, 8.2 Hz, 1H, 4'-H); 1.76 (s, 3H, 8'-$CH_3$); 1.60 (s, 3H, 12a-$CH_3$).

12a-Hydroxymethylrotenone: Rotenone (394 mg, 1 mmol) and paraformaldehyde (300 mg, excess) in dry DMF (4 mL) was heated at 150° C. for 24 h. Cooled to RT, added water (10 mL) and extracted with ether (3×15 mL). The crude product was purified on silica gel column usinf EtOAc:Hexane (3:1) as eluent to obtain the hydroxymethylrotenone as colorless oil (344 mg, mixture of isomers, 81%). The two isomers (isomer A 90 mg+isomer B 112 mg) were separated on column. $^1$H NMR ($CDCl_3$) (mixture of isomers): δ 7.86 (d, J=8.4 Hz, 1H, 11-H); 6.70 (s, 1H, 1-H); 6.54 (d, J=8.4 Hz, 1H, 10-H); 6.50 (s, 1H, 4-H); 5.34 (dd, 1H, J=9.5, 8.3 Hz, 5'-H); 5.20 (s, 1H, 7'-H); 5.10 (s, 1H, 7'-H); 4.99 (1H, bs, 6a-H); 4.60-4.40 (m, 3H, 6H-b, 12a-CH2); 3.78 (d, J=11.3 Hz, 1H, 6-Ha); 3.88 (s, 3H, $OCH_3$); 3.85 (s, 3H, $CH_3$); 3.39 (dd, J=15.5, 9.6 Hz, 1H, 4'-H); 3.04 (dd, J=15.5, 8.0 Hz, 1H, 4'-H); 1.83 (s, 3H, 12a-$CH_3$).

Isomer A: 7.94 (d, J=8.4 Hz, 1H, 11-H); 7.75 (s, 1H, 1-H); 6.52 (d, J=8.4 Hz, 1H, 10-H); 6.40 (s, 1H, 4-H); 5.20 (dd, J=9.8, 8.2 Hz, 1H, 5'-H); 5.08 (s, 1H, 7'-H); 5.00 (s, 1H, 7'-H); 4.85-4.75 (m, 2H, 12a-CH2); 4.40 (dd, J=9.8, 8.2 Hz, 1H, 6-Ha); 3.98 (d, J=11.3 Hz, 1H, 6-Ha); 3.88 (s, 3H, $OCH_3$); 3.85 (s, 3H, $CH_3$); 3.39 (dd, J=15.5, 9.6 Hz, 1H, 4'-H); 2.95 (dd, J=15.5, 8.0 Hz, 1H, 4'-H); 1.86 (s, 3H, 12a-$CH_3$).

Isomer B: 7.87 (d, J=8.4 Hz, 1H, 11-H); 6.73 (s, 1H, 1-H); 6.44 (d, J=8.4 Hz, 1H, 10-H); 6.40 (s, 1H, 4-H); 5.24 (m, 2H, 5'-H and 6a-H); 5.02 (s, 1H, 7'-H); 5.00 (s, 1H, 7'-H); 4.82-4.44 (m, 4H, 6-Ha, 6-Hb, 12a-CH2); 3.78 (d, J=11.3 Hz, 1H, 6-Ha); 3.88 (s, 3H, $OCH_3$); 3.85 (s, 3H, $CH_3$); 3.39 (dd, J=15.5, 9.6 Hz, 1H, 4'-H); 2.95 (dd, J=15.5, 8.0 Hz, 1H, 4'-H); 1.82 (s, 3H, 12a-$CH_3$).

12a-Hydroxymethylrotenone tosylate: A mixture of tosylchloride (190 mg, 1 mmol), hydroxymethylrotenone (212 mg, 0.5 mmol) and pyridine (1 mL) in dry $CH_2Cl_2$ (5 mL) was stirred at 0° C. for 24 h under argon. Evaporated the solvent and purified by column chromatography on silica gel using EtOAc:Hexane (1:1) to obtain the tosylate as colorless solid (194 mg, 67%). $^1$H NMR ($CDCl_3$): δ 7.84 (m, 3H, 11-H, 2CH); 7.35 (d, J=7.6 Hz, 2H, 2CH); 6.83 (s, 1H, 1-H); 6.45 (d, J=8.4 Hz, 1H, 10-H); 6.40 (s, 1H, 4-H); 5.24-4.40 (m, 8H, 5'-H, 6a-H, 7'-H, 6-Ha, 6-Hb, 12a-CH2F, 6-Ha); 3.82 (s, 3H, $OCH_3$); 3.80 (s, 3H, $CH_3$); 3.39 (dd, J=15.5, 9.6 Hz, 1H, 4'-H); 2.95 (dd, J=15.5, 8.0 Hz, 1H, 4'-H); 2.42 (s, 3H, Ts$CH_3$); 1.81 (s, 3H, 12a-$CH_3$) (mixture of isomers).

12a-Fluoromethylrotenone: Method A (4-NE-39): The tosylate (58 mg, 0.1 mmol) and TBAF (0.125 mL, 0.125 mmol) in dry THF (1 mL) was heated at 60° C. for 12 h. Evaporated the solvent and the residue was purified by chromatography on silica gel using EtOAc:Hexane (3:7) to obtain the fluoride as glassy solid (ca 8 mg, impure!). The reaction was complete when used 1.5 equivalents of solid TBAF.

Method B (4-NE-40): Rotenone (394 mg, 1 mmol) was dissolved in dry DMF (2 mL) and cooled to 0° C. under argon atmosphere. Sodium hydride (50 mg, excess) was added with caution and stirred for 15 minutes at 0° C. Added bromofluoromethane (0.5 mL, excess) and the reaction mixture was heated at 150° C. for 24 h. Cooled to RT, added water (10 mL) and extracted with ether (3×15 mL). The crude product was purified on silica gel column usinf EtOAc:Hexane (1:1) as eluent to obtain the fluoromethylrotenone as colorless solid (64 mg, impure).

Method C (4-NE-38): Hydroxymethyl rotenone (100 mg, 0.23 mmol) was dissolved in dry $CH_2Cl_2$ (mL) and cooled to 0° C. under argon. DAST (46 mg, 0.3 mmol) was added dropwise and the mixture was stirred at 0° C. for 2 h. Evaporated the volatiles and the crude yellow residue was purified on silica gel chromatography using EtOAc:Hexane (2:3) to obtain the fluoride as colorless glassy solid (52 mg, 53%). $^1$H NMR (CDCl$_3$): δ 7.92 (d, J=8.4 Hz, 1H, 11-H); 6.83 (s, 1H, 1-H); 6.45 (d, J=8.4 Hz, 1H, 10-H); 6.40 (s, 1H, 4-H); 5.24-4.40 (m, 8H, 5'-H, 6a-H, 7'-H, 6-Ha, 6-Hb, 12a-CH2F, 6-Ha); 3.82 (s, 3H, OCH3); 3.80 (s, 3H, CH3); 3.39 (dd, J=15.5, 9.6 Hz, 1H, 4'-H); 2.95 (dd, J=15.5, 8.0 Hz, 1H, 4'-H); 1.81 (s, 3H, 12a-CH3).

Chloroacetate: Wittig salt (471 mg, 1.2 mmol) was suspended in dry THF (10 mL) and cooled to 0° C. in an ice bath under argon atmosphere. A solution of (TMS)$_2$NNa (1 M solution in THF, 1.1 mL, 1.1 mmol) was added dropwise and the mixture was stirred for 15 minutes at 0° C. The suspension got dissolved in to an yellow-orange solution. The solution was cooled to −78° C. and a solution of ketoacetate (440 mg, 1 mmol) was added dropwise. Reaction mixture stirred at −78° C. for 2 h and then allowed to come to room temperature. Added water (25 mL) and extracted with dichloromethane (3×25 mL). The organic extracts were collected, washed with brine and evaporated to get a brown syrup which was purified by flash column chromatography on silica gel using EtOAc:hexane (1:4) to afford the chloroacetate (E/Z ratio=1:1) as colorless solid (340 mg, 72%); m. p.: 122-125° C.; $^1$H NMR (CDCl$_3$): δ 7.06 (d, J=7.98 Hz, 1H, 11-H); 6.63 (s, 1H, 1-H); 6.42 (d, J=7.98 Hz, 1H, 10-H); 6.40 (s, 1H, 4-H); 6.27 (d, J=4.26 Hz, 1H, 12-H), 6.39, 6.02 (2s, 1H, 7'-H, mixture of e/z isomers); 5.82, 5.22 (2dd, J=6.68, 9.42 Hz, 5'-H, mixture of e/z isomers); 4.96 (ddd, J=5.74, 5.98, 11.26 Hz, 1H, 6a-H); 4.43 (m, 1H, 6'-Hβ); 4.22 (m, 1H, 6'-Hα); 3.82 (s, 6H, 2×OCH$_3$); 3.27 (m, 1H, 12a-H); 3.22, 3.16 (2dd, J=6.22, 9.78 Hz, 1H, 4'-Hβ); 2.99, 2.82 (2dd, J=8.20, 16.38 Hz, 1H, 4'-Hα); 1.90 (2s, 3H, 8'-CH$_3$); 1.78 (s, OAc); $^{13}$C NMR (CDCl$_3$): δ 170.04 (C=O of OAc); 162.12 (C-9); 161.69 (C-7a); 149.87, 149.78 (C-3); 149.36 (C-4a); 148.58 (C-12); 143.45 (C-2); 141.18, 140.19 (C-6'); 131.21 (C-11); 112.71 (C-11a); 112.20, 111.71 (C-8); 111.47, 111.29 (C-7'); 108.54 (C-1); 105.73 (C-10); 102.98, 101.95 (C-12b); 100.11 (C-4); 86.30, 83.14 (C-5'); 69.01, 66.59 (C-6a); 64.53 (C-6); 56.40 (OCH$_3$); 55.86 (OCH$_3$); 36.47 (C-12a); 31.80, 31.59 (C-4'); 20.88 (COCH3) 17.08, 14.91 (C-8').

Fluoroacetate: Wittig salt (400 mg, 1.2 mmol) was suspended in dry THF (10 mL) and cooled to 0° C. in an ice bath under argon atmosphere. A solution of (TMS)$_2$NNa (1 M solution in THF, 1.2 mL, 1.2 mmol) was added dropwise and the mixture was stirred for 15 minutes at 0° C. The suspension got dissolved in to an yellow-orange solution. The solution was cooled to −78° C. and a solution of ketoacetate (438 mg, 1 mmol) in THF (3 mL) was added dropwise. Reaction mixture was stirred at −78° C. for 1 h and then allowed to come to room temperature. Added water (25 mL) and extracted with dichloromethane (3×25 mL). The organic extracts were collected, washed with brine and evaporated to get a brown syrup which was purified by flash column chromatography on silica gel using EtOAc:hexane (1:4) to afford the fluoroacetate (Z/E ratio=40:60) as colorless solid (347 mg, 76%); $^1$H NMR (CDCl$_3$): δ 7.07 (d, J=7.98 Hz, 1H, 11-H); 6.62 (s, 1H, 1-H); 6.41 (d, J=7.98 Hz, 1H, 10-H); 6.40 (s, 1H, 4-H); 6.26 (d, J=4.40 Hz, 1H, 12-H), 6.65, 6.20 (2d, J=85 Hz, 1H, 7'-H); 5.85, 5.08 (2dd, J=6.68, 9.42 Hz, 5'-H); 4.94 (ddd, J=5.74, 5.98, 11.26 Hz, 1H, 6a-H); 4.43 (m, 1H, 6'-Hβ); 4.23 (m, 1H, 6'-Hα); 3.82 (s, 6H, 2×OCH$_3$); 3.28 (m, 1H, 12a-H); 3.24, 3.22 (2dd, J=6.22, 9.78 Hz, 1H, 4'-Hβ); 2.99, 2.96 (2dd, J=8.20, 16.38 Hz, 1H, 4'-Hα); 1.78 (s, OAc); 1.71 (dd, J=0.88, 1.77 Hz), 1.69 (dd, J=1.11, 2.87 Hz, 3H, 8'-CH$_3$); $^{13}$C NMR (CDCl$_3$): δ 169.97, 162.11, 161.92, 149.79, 149.73, 149.37, 148.57, 147.58, 145.72, 145.01, 143.47, 143.15, 131.12, 118.12, 118.05, 112.86, 112.66, 11.76, 111.29, 111.13, 108.58, 102.88, 100.11, 82.95, 82.84, 77.89, 77.80, 69.06, 69.03, 66.62, 66.59, 64.53, 56.39, 55.83, 36.49, 31.23, 31.09, 20.85, 9.39, 9.34, 7.36, 7.30; MS (m/z, %): 456 (28); 397 (42); 286 (5); 192 (100); 179 (120; 154 (34).

Fluororotenol: Fluoroacetate (456 mg, 1 mmol) was dissolved in minimum amount of $CH_2Cl_2$ (1 mL) and added a 1:1 mixture of MeOH:H$_2$O (10 mL) followed by solid potassium carbonate (500 mg, 5 mmol). The mixture was heated at 60° C. for 4 h with vigorous stirring. Cooled to room temp, added more water (25 mL) and extracted with $CH_2Cl_2$ (3×25 mL). The organic extracts were collected, washed with brine, dried over anhydrous Na$_2$SO$_4$, filtered and evaporated to get a syrup which was purified by flash column chromatography on silica gel using EtOAc:hexane (2:3) to afford the fluoroalcohol as white solid (389 mg, 94%); m. p.: 144-146° C. (turned brown); $^1$H NMR (CDCl$_3$): δ 7.05 (d, J=7.96 Hz, 1H, 11-H); 6.71 (s, 1H, 1-H); 6.46 (s, 1H, 4-H); 6.43 (dd, J=2.21, 5.75 Hz, 1H, 10-H); 6.74, 6.44 (2d, J=85.9 Hz, 1H, 7'-H); 5.87, 5.15 (2dd, J=8.45, 9.07 Hz, 1H, 5'-H); 4.92 (d, J=3.32 Hz, 1H, 12-H); 4.83 (ddd, J=5.53, 5.53, 11.15 Hz, 1H, 6a-H); 4.62 (dd, J=10.18, 10.83 Hz, 1H, 6'-Hβ); 4.23 (dd, J=5.08, 9.73 Hz, 1H, 6'-Hα); 3.86 (s, 3H, OCH$_3$); 3.84 (s, 3H, OCH$_3$); 3.31, 3.25 (2dd, J=5.97, 15.78 Hz, 1H, 4'-Hβ); 3.39 (dd, J=4.86, 5.09 Hz, 1H, 12a-H); 3.01, 2.95 (2dd, J=7.96, 15.70 Hz, 1H, 4'-Hα); 1.91 (dd, J=0.88, 1.77 Hz), 1.90 (dd, J=1.1, 2.87 Hz, 3H, 8'-CH$_3$); $^{13}$C NMR (CDCl$_3$): d 171.22, 161.62, 161.44, 149.47, 149.27, 149.23, 149.17, 147.53, 145.69, 144.97, 143.62, 143.12, 130.34, 118.23, 118.15, 114.45, 114.31, 112.79, 112.59, 111.64, 109.02, 102.47, 100.51, 82.80, 82.69, 69.38, 66.35, 65.05, 0.40, 56.52, 55.69, 38.04, 31.27, 31.11, 20.96, 14.16, 9.39, 9.32, 7.35, 7.30; MS (m/z, %): 414 (22); 397 (38); 192 (100); 177 (10); 154 (36).

Fluororotenol: Fluoroacetate (456 mg, 1 mmol) was dissolved in minimum amount of $CH_2Cl_2$ (1 mL) and added a 1:1 mixture of MeOH:H$_2$O (10 mL) followed by solid potassium carbonate (500 mg, 5 mmol). The mixture was heated at 60° C. for 4 h with vigorous stirring. Cooled to room temp, added more water (25 mL) and extracted with $CH_2Cl_2$ (3×25 mL). The organic extracts were collected, washed with brine, dried over anhydrous Na$_2$SO$_4$, filtered and evaporated to get a syrup which was purified by flash column chromatography on silica gel using EtOAc:hexane (2:3) to afford the fluoroalcohol as white solid (389 mg, 94%); m. p.: 144-146° C. (turned brown); $^1$H NMR (CDCl$_3$): δ 7.05 (d, J=7.96 Hz, 1H, 11-H); 6.71 (s, 1H, 1-H); 6.46 (s, 1H, 4-H); 6.43 (dd, J=2.21, 5.75 Hz, 1H, 10-H); 6.74, 6.44 (2d, J=85.9 Hz, 1H, 7'-H); 5.87, 5.15 (2dd, J=8.45, 9.07 Hz, 1H, 5'-H); 4.92 (d, J=3.32 Hz, 1H, 12-H); 4.83 (ddd, J=5.53, 5.53, 11.15 Hz, 1H, 6a-H); 4.62 (dd, J=10.18, 10.83 Hz, 1H, 6'-Hβ); 4.23 (dd, J=5.08, 9.73 Hz, 1H, 6'-Hα); 3.86 (s, 3H, OCH$_3$); 3.84 (s, 3H, OCH$_3$); 3.31, 3.25 (2dd, J=5.97, 15.78 Hz, 1H, 4'-Hβ); 3.39 (dd, J=4.86, 5.09 Hz, 1H, 12a-H); 3.01, 2.95 (2dd, J=7.96, 15.70 Hz, 1H, 4'-Hα); 1.91 (dd, J=0.88, 1.77 Hz), 1.90 (dd, J=1.1, 2.87 Hz, 3H, 8'-CH$_3$); $^{13}$C NMR (CDCl$_3$): d 171.22, 161.62, 161.44, 149.47, 149.27, 149.23, 149.17, 147.53, 145.69, 144.97, 143.62, 143.12, 130.34, 118.23, 118.15, 114.45, 114.31, 112.79, 112.59, 111.64, 109.02, 102.47, 100.51, 82.80, 82.69, 69.38, 66.35, 65.05, 0.40, 56.52, 55.69, 38.04, 31.27, 31.11, 20.96, 14.16, 9.39, 9.32, 7.35, 7.30; MS (m/z, %): 414 (22); 397 (38); 192 (100); 177 (10); 154 (36).

Methylrotenol: Trimethyltinrotenol (25 mg, 0.05 mmol), Pd(PPh$_3$)$_4$ (6 mg, 0.005 mmol), triphenylphosphine (1.5 mg, 0.005 mmol), copper iodide (1.0 mg, 0.005 mmol) and potassium carbonate (0.7 mg, 0.005 mmol) were mixed together in dry DMF (0.5 mL) under argon and was stirred for 2 minutes at room temperature. Added methyl iodide (64 mg, 28 µL, 4.5 mmol) in one portion and the mixture was stirred at room temperature for 5 minutes followed by 60° C. for 5 minutes and 80° C. for 15 minutes. The starting material was completely consumed. The reaction mixture was cooled to room temperature, added water (2 mL) and extracted with ether (3×2 mL). Evaporation of the solvent gave a residue which was purified by flash column chromatography on silica gel using EtOAc:Hexane (5:7) to furnish the methyl rotenol as colorless sticky solid (16 mg, 78%); $^1$H NMR (CDCl$_3$): δ 7.05 (d, J=7.96 Hz, 1H, 11-H); 6.67 (s, 1H, 1-H); 6.44 (s, 1H, 4-H); 6.42 (d, J=7.74 Hz, 10-H); 5.78 (dd, J=8.84, 9.51, 1H, 5'-H); 5.43 (q, J=5.75 Hz, 1H, 7'-H); 4.96 (bs, 1H, 12-H); 4.84 (ddd, J=5.75, 5.53, 11.05 Hz, 1H, 6a-H); 4.62 (t, J=10.83 Hz, 1H, 6-Hβ); 4.24 (dd, J=5.08, 4.65 Hz, 1H, 6-Hα); 3.83 (s, 3H, OCH$_3$); 3.82 (s, 3H, OCH$_3$); 3.50 (m1H, 12a-H); 3.26 (dd, J=5.97, 9.28 Hz, 1H, 4'-Hβ); 2.96 (dd, J=8.84, 7.30 Hz, 1H, 4'-Hα); 1.72, 1.69, 1.67 (3s, 9H, OAc, 8'-CH$_3$, 9'-CH$_3$); $^{13}$C NMR (100 MHz, CDCl$_3$): δ 162.16, 149.68, 149.36, 149.14, 143.88, 134.59, 130.39, 123.25, 113.63, 113.36, 111.34, 108.83, 102.75, 100.74, 81.29, 70.85, 69.17, 66.33, 65.06, 56.57, 55.89, 38.12, 31.35, 17.26, 13.07; MS (m/z, %): 411 (M+1, 10); 410 (26); 393 (45); 307 (8); 192 (100).

Methylrotenol acetate: Wittig salt (113 mg, 0.27 mmol) was suspended in dry THF (3 mL) and cooled to 0° C. in an ice bath under argon atmosphere. A solution of (TMS)$_2$NNa (1 M solution in THF, 0.25 mL, 0.25 mmol) was added dropwise and the mixture was stirred for 15 minutes at 0° C. The suspension got dissolved in to an yellow-orange solution. The solution was cooled to −78° C. and a solution of ketoacetate (100 mg, 0.23 mmol) was added dropwise. Reaction mixture stirred at −78° C. for 4 h and then allowed to come to room temperature. Added water (10 mL) and extracted with dichloromethane (3×10 mL). The organic extracts were collected, washed with brine and evaporated to get a brown syrup which was purified by flash column chromatography on silica gel using EtOAc:hexane (1:4) to afford the olefin as colorless liquid (78 mg, 75%); $^1$H NMR (CDCl$_3$): δ 7.09 (d, J=7.96 Hz, 1H, 11-H); 6.66 (s, 1H, 1-H); 6.42 (d, J=7.74 Hz, 10-H); 6.41 (s, 1H, 4-H); 6.30 (d, J=4.42 Hz, 1H, 12-H); 5.74 (dd, J=8.84, 9.51, 1H, 5'-H); 5.45 (q, J=5.75 Hz, 1H, 7'-H); 4.88 (ddd, J=5.75, 5.53, 11.05 Hz, 1H, 6a-H); 4.48 (t, J=10.83 Hz, 1H, 6-Hβ); 4.26 (dd, J=5.08, 4.65 Hz, 1H, 6-Hα); 3.84 (s, 6H, 2×OCH$_3$); 3.55 (ddd, J=6.85, 5.75, 10.83 Hz, 1H, 12a-H); 3.25 (dd, J=5.97, 9.28 Hz, 1H, 4'-Hβ); 2.93 (dd, J=8.84, 7.30 Hz, 1H, 4'-Hα); 1.75, 1.71, 1.69 (3s, 9H, OAc, 8'-CH$_3$, 9'-CH$_3$); MS (m/z, %): 411 (M+1, 10); 410 (26); 393 (50); 192 (100).

REFERENCES

The following references, to the extent that they provide exemplary procedural or other details supplementary to those set forth herein, are specifically incorporated herein by reference.

Blandini and Greenamyre, Analytical Biochem., 230:16-19, 1995.
Charalambous et al., Nucl. Med. Biol., 22:65-69, 1995.
Enas et al., J. Labelled Compd. Radiopharm., 37:220-222, 1995.
Greene and Wuts, In: Protective Groups in Organic Synthesis, 2$^{nd}$ Ed.; Wiley, N.Y., 1991.
Kenski et al., J. Labelled Compd. Radiopharm., 42(1):S333-335, 1999.
March, In: Advanced Organic Chemistry, McGraw Hill Book Co., NY, 251-259, 1977.
Marshall et al., Circulation, 82:998-1007, 1990.
Marshall et al., J. Nucl. Med., 32:1979-1988, 1991.
Marshall et al., J. Nucl. Med., 42:272-281, 2001.
O'Neil et al., In: [F-18] Fluororotenoids: Evaluation of Potential Myocardial Imaging Agents in an Isolated, Perfused Rabbit Heart Model, 19th Annual Western Reg. Mtg., Soc. of Nuc. Med., Monterey, Calif., 1994.
VanBrocklin et al., J. Labelled Compd. Radiopharm., 37:217-219, 1995.
VanBrocklin et al., J. Nucl. Med., 35(5):73P, 1994.

What is claimed is:

1. A compound having the following structure:

[Chemical structure diagram]

wherein X is independently the same or different and is selected for the group consisting of O and S, X$_1$ is selected from the group consisting of SnMe$_3$, SnBu$_3$, B(—OCH$_2$C(CH$_3$)$_2$CH$_2$O—), BF$_3$K, ZnI, ZnBr, Br, Cl, F, CH$_2$F, CH$_2$CH$_2$F, C$_6$H$_4$F, and CH$_2$C$_6$H$_4$F; and X$_2$ is selected from the group consisting of O and S; and R is independently the same or different and is selected from the group consisting of H, lower alkyl, and a halogen; and R' is independently the same or different and is a lower alkyl; and R" is independently the same or different and is selected from the group consisting of H and a lower alkyl; and R$_3$ is independently the same or different and is selected from the group consisting of H, lower alkyl, and CH$_2$F;

and wherein the stereochemical configuration at any stereocenter of the compound is R, S or a mixture of these configurations.

2. The compound of claim 1, wherein X$_1$ is F.

3. The compound of claim 2, wherein the F is $^{18}$F or $^{19}$F.

4. The compound of claim 1, wherein X$_1$ is Br.

5. The compound of claim 4, wherein the Br is $^{75}$Br, $^{76}$Br, $^{77}$Br, $^{79}$Br, $^{80}$Br, $^{80m}$Br, or $^{81}$Br.

6. A composition comprising the compound of any one of claim 3 or 5 and a pharmaceutically acceptable excipient.

7. A method of imaging a region in a patient, comprising:
administering to the patient a diagnostically effective amount of the composition of claim 6, and
detecting radiation in a region of the patient, and
obtaining an image of the region of the patient.

8. The method of claim 7, wherein the region of the patient is the heart.

9. A compound having the following structure:

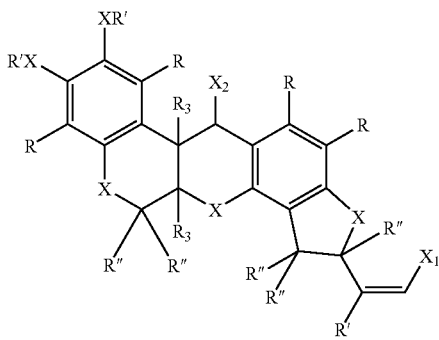

wherein X is independently the same or different and is selected from the group consisting of O and S, and wherein at least one X is S;

X₁ is selected from the group consisting of SnMe₃, SnBu₃, B(—OCH₂C(CH₃)₂CH₂O—), BF₃K, ZnI, ZnBr, Br, Cl, I, F, CH₂F, CH₂CH₂F, C₆H₄F, and CH₂C₆H₄F;

X₂ is selected from the group consisting of O and S;

R is independently the same or different and is selected from the group consisting of H, lower alkyl, and a halogen;

R' is independently the same or different and is a lower alkyl;

R" is independently the same or different and is selected from the group consisting of H and a lower alkyl;

R₃ is independently the same or different and is selected from the group consisting of H, lower alkyl, and CH₂F; and wherein the stereochemical configuration at any stereocenter is R, S or a mixture of these configurations.

10. The compound of claim 9, wherein X₁ is F.
11. The compound of claim 10, wherein the F is ¹⁸F or ¹⁹F.
12. The compound of claim 9, wherein X₁ is Br.
13. The compound of claim 12, wherein the Br is ⁷⁵Br, ⁷⁶Br, ⁷⁷Br, ⁷⁹Br, ⁸⁰BR, ⁸⁰mBr, or ⁸¹Br.
14. The compound of claim 9, wherein X₁ is I.
15. The compound of claim 14, wherein the I is ¹²³I, ¹²⁵I, ¹³¹I, ¹²⁴I, ¹²⁷I, or ¹²²I.
16. A composition comprising the compound of any one of claim 11, 13 or 15 and a pharmaceutically acceptable excipient.
17. A method of imaging a region in a patient, comprising: administering to the patient a diagnostically effective amount of the composition of claim 16, and detecting radiation in a region of the patient, and obtaining an image of the region of the patient.
18. The method of claim 17, wherein the region of the patient is the heart.
19. A compound having the structure:

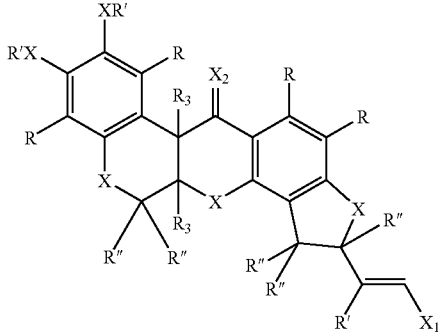

wherein X is independently the same or different and is selected for the group consisting of O and S, X₁ is selected from the group consisting of SnMe₃, SnBu₃, B(—OCH₂C(CH₃)₂CH₂O—), BF₃K, ZnI, ZnBr, Br, I, F, CH₂F, CH₂CH₂F, C₆H₄F, and CH₂C₆H₄F; and X₂ is selected from the group consisting of O and S; and R is independently the same or different and is selected from the group consisting of H, lower alkyl, and a halogen; and R' is independently the same or different and is a lower alkyl; and R" is independently the same or different and is selected from the group consisting of H and a lower alkyl; and R₃ is independently the same or different and is selected from the group consisting of H, lower alkyl, and CH₂F;

and wherein the stereochemical configuration at any stereocenter of the compound is R, S or a mixture of these configurations.

20. The compound of claim 19, wherein X₁ is I.
21. The compound of claim 20, wherein the I is ¹²³I, ¹²⁵I, ¹³¹I, ¹²⁴I, ¹²⁷I, or ¹²²I.
22. The compound of claim 19, wherein X₁ is F.
23. The coumpound of claim 22, wherein the F is ¹⁸F or ¹⁹F.
24. The compound of claim 19, wherein X₁ is Br.
25. The compound of claim 24, wherein the Br is ⁷⁵Br, ⁷⁶Br, ⁷⁷Br, ⁷⁹Br, ⁸⁰Br, ⁸⁰mBr, or ⁸¹Br.
26. A composition comprising the compound of any one of claim 21, 23 or 25 and a pharmaceutically acceptable excipient.
27. A method of imaging a region in a patient, comprising: administering to the patient a diagnostically effective amount of the composition of claim 26, and detecting radiation in a region of the patient, and obtaining an image of the region of said patient.
28. The method of claim 27, wherein the region is the heart.
29. A compound having the structure:

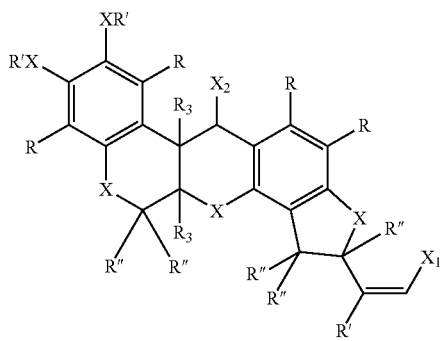

wherein X is independently the same or different and is selected from the group consisting of O and S;

X₁ is selected from the group consisting of SnMe₃, SnBu₃, B(—OCH₂C(CH₃)₂CH₂O—), BF₃K, ZnI, ZnBr, Br, Cl, F, CH₂F, CH₂CH₂F, C₆H₄F, and CH₂C₆H₄F;

X₂ is selected from the group consisting of OR, OH, OPg, SH, SR, and SPg, wherein Pg is a protecting group;

R is independently the same or different and is selected from the group consisting of H, lower alkyl, and a halogen;

R' is independently the same or different and is a lower alkyl;

R" is independently the same or different and is selected from the group consisting of H and lower alkyl; and $R_3$ is independently the same or different and is selected from the group consisting of H, lower alkyl, and $CH_2F$; and wherein the stereochemical configuration at any stereocenter of the compound is represented is R, S, or a mixture of these configurations.

30. A compound having the structure:

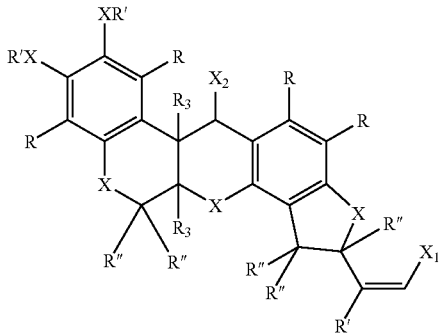

wherein X is independently the same or different and is selected from the group consisting of O and S, and further wherein at least one X is S;

$X_1$ is selected from the group consisting of $SnMe_3$, $SnBu_3$, $B(—OCH_2C(CH_3)_2CH_2O—)$, $BF_3K$, ZnI, ZnBr, Br, Cl, I, F, $CH_2F$, $CH_2CH_2F$, $C_6H_4F$, and $CH_2C_6H_4F$;

$X_2$ is selected from the group consisting of OH, OR, OPg, SH, SR, and SPg, wherein Pg is a protecting group;

R is independently the same or different and is selected from the group consisting of H, lower alkyl, and a halogen;

R' is independently the same or different and is a lower alkyl;

R" is independently the same or different and is selected from the group consisting of H and a lower alkyl; and $R_3$ is independently the same or different and is selected from the group consisting of H, lower alkyl, and $CH_2F$; and wherein the stereochemical configuration at any stereocenter is R, S or a mixture of these configurations.

31. A compound having the structure:

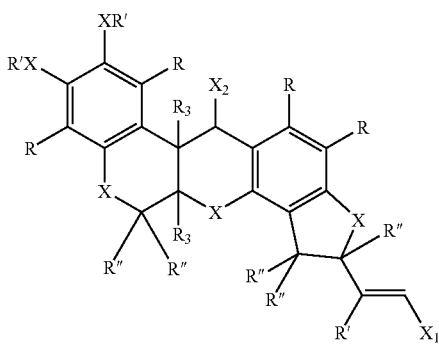

wherein X is independently the same or different and is selected from the group consisting of O and S;

$X_1$ is selected from the group consisting of $SnMe_3$, $SnBu_3$, $B(—OCH_2C(CH_3)_2CH_2O—)$, $BF_3K$, ZnI, ZnBr, Br, Cl, I, F, $CH_2F$, $CH_2CH_2F$, $C_6H_4F$, and $CH_2C_6H_4F$;

$X_2$ is selected from the group consisting of OH, OR, OPg, SH, SR, and SPg, wherein Pg is a protecting group;

R is independently the same or different and is selected from the group consisting of H, lower alkyl, and halogen;

R' is independently the same or different and is a lower alkyl;

R" is independently the same or different and is selected from the group consisting of H and lower alkyl; and $R_3$ is independently the same or different and is selected from the group consisting of H, lower alkyl, and $CH_2F$; and wherein the stereochemical configuration at any stereocenter is R, S or a mixture of these configurations.

32. A compound having the structure:

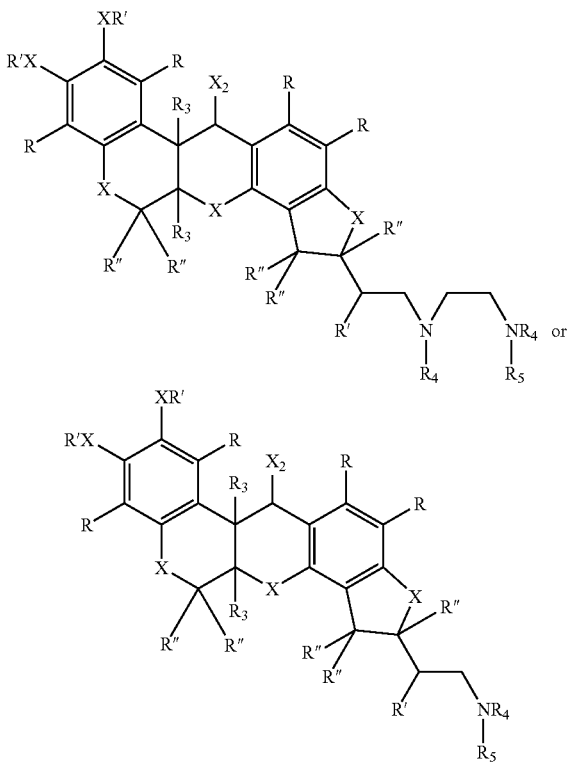

wherein X is independently the same or different and is selected from the group consisting of O and S;

$X_2$ is selected from the group consisting of OH, OR, OPg, SH, SR, SPg, =O, and =S, wherein Pg is a protecting group;

R is independently the same or different and is selected from the group consisting of H, lower alkyl, and halogen;

R' is independently the same or different and is a lower alkyl;

R" is independently the same or different and is selected from the group consisting of H and lower alkyl;

$R_3$ is independently the same or different and is selected from the group consisting of H, lower alkyl, and $CH_2F$; and $R_4$ is independently the same or different and is selected from the group consisting of H, alkyl, and aryl; and $R_5$ is selected from the group consisting of $CH_2CH(OH)$ $CH_2F$, $CH_2C_6H_4F$, $COC_6H_4F$, and $CH_2CH_2F$; and wherein the stereochemical configuration at any stereocenter is R, S or a mixture of these configurations.

33. A compound having the structure:

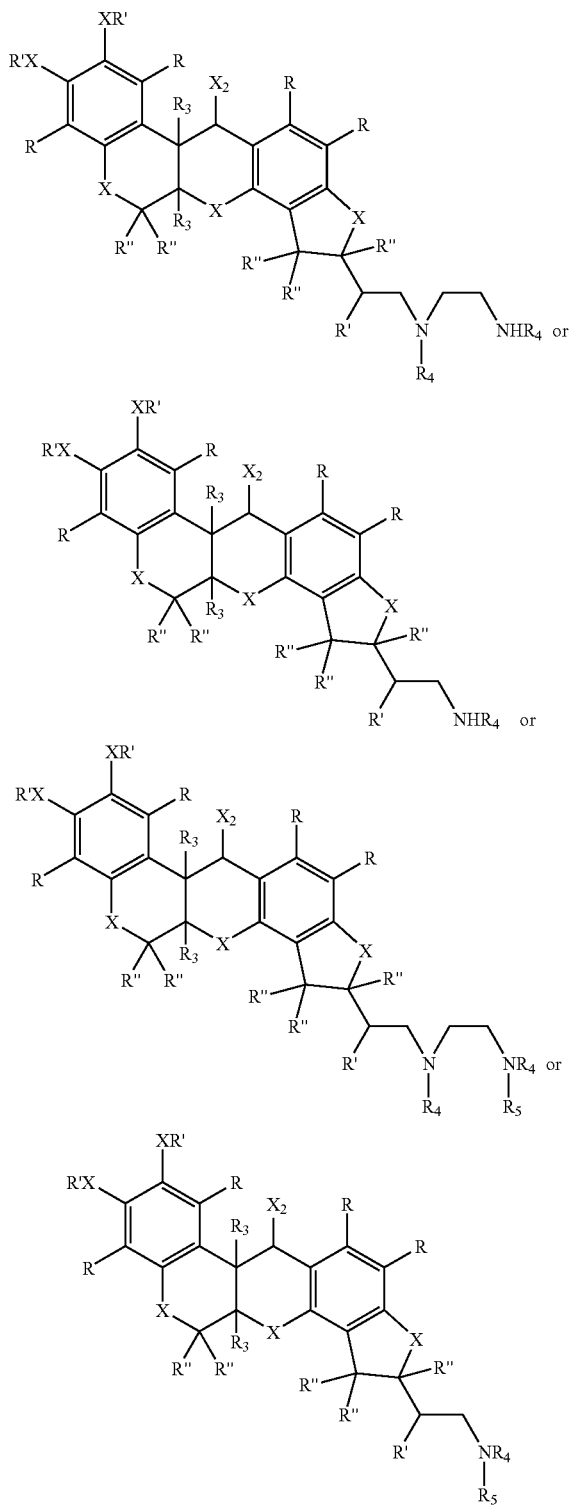

wherein X is independently the same or different and is selected from the group consisting of O and S;

$X_2$ is selected from the group consisting of OH, OR, OPg, SH, SR, SPg, =O, and =S, wherein Pg is a protecting group;

R is independently the same or different and is selected from the group consisting of H, lower alkyl, and halogen;

R' is independently the same or different and is a lower alkyl;

R" is independently the same or different and is selected from the group consisting of H and lower alkyl;

$R_3$ is independently the same or different and is selected from the group consisting of H, lower alkyl, and $CH_2F$; and $R_4$ is independently the same or different and is selected from the group consisting of H, alkyl, and aryl; and $R_5$ is selected from the group consisting of $^{11}CH_3$ and $^{11}CH_3CH_2$; and wherein the stereochemical configuration at any stereocenter is R, S or a mixture of these configurations.

34. A compound having the structure:

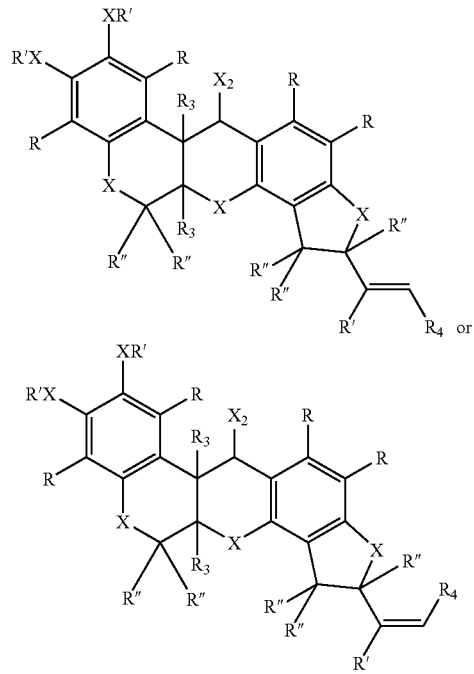

wherein X is independently the same or different and is selected from the group consisting of O and S;

$X_2$ is selected from the group consisting of OH, OR, OPg, SH, SR, SPg, =O, and =S, wherein Pg is a protecting group;

R is independently the same or different and is selected from the group consisting of H, lower alkyl, and halogen;

R' is independently the same or different and is a lower alkyl;

R" is independently the same or different and is selected from the group consisting of H and lower alkyl;

$R_3$ is independently the same or different and is selected from the group consisting of H, lower alkyl, and $CH_2F$; and $R_4$ is selected from the group consisting of $^{11}CH_3$, $^{12}CH_3$, $^{11}CH_3CH_2$, and $^{12}CH_3CH_2$; and wherein the stereochemical configuration at any stereocenter is R, S or a mixture of these configurations.

35. A compound having the structure:

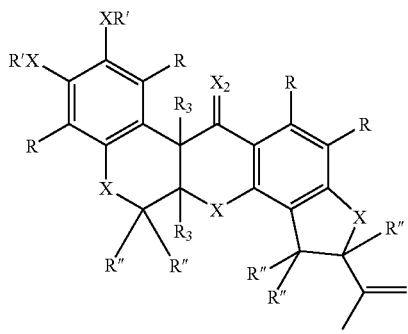

wherein X is independently the same or different and is selected from the group consisting of O and S;
$X_2$ is selected from the group consisting of O and S;
R is independently the same or different and is selected from the group consisting of H, lower alkyl, and halogen;
R' is independently the same or different and is a lower alkyl;
R" is independently the same or different and is selected from the group consisting of H and lower alkyl; and
$R_3$ is selected from the group consisting of $^{11}CH_3$, $^{11}CH_3CH_2$, and $^{12}CH_3CH_2H_2F$; and
wherein the stereochemical configuration at any stereocenter is R, S or a mixture of these configurations.

36. A compound having the structure:

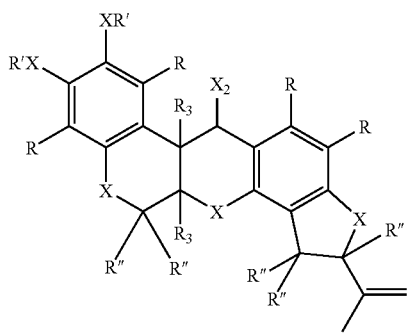

wherein X is independently the same or different and is selected from the group consisting of O and S;
$X_2$ is selected from the group consisting of OH, OR, OPg, SH, SR, and SPg, wherein Pg is a protecting group;
R is independently the same or different and is selected from the group consisting of H, lower alkyl, and halogen;
R' is independently the same or different and is a lower alkyl;
R" is independently the same or different and is selected from the group consisting of H and lower alkyl;
$R_3$ is selected from the group consisting of $^{11}CH_3$, $^{12}CH_3$, $^{11}CH_3CH_2$, and $^{12}CH_3CH_2$; and
wherein the stereochemical configuration at any stereocenter is R, S or a mixture of these configurations.

37. A compound having the structure:

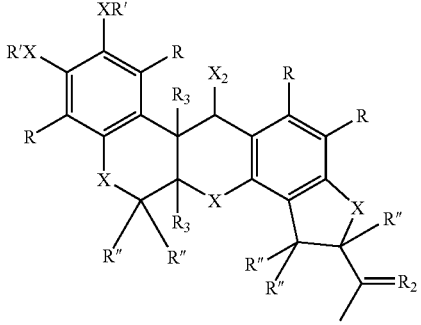

wherein X is independently the same or different and is selected from the group consisting of O and S;
$X_2$ is selected from the group consisting of OH, OR, OPg, SH, SR, SPg, =O, and =S, wherein Pg is a protecting group;
R is independently the same or different and is selected from the group consisting of H, lower alkyl, and halogen;
R' is independently the same or different and is a lower alkyl;
R" is independently the same or different and is selected from the group consisting of H and lower alkyl;
$R_2$ is selected from the group consisting of $^{11}CH_3$, $^{12}CH_3$, $^{11}CH_3CH_2$, and $^{12}CH_3CH_2$; and
$R_3$ is independently the same or different and is selected from the group consisting of H, lower alkyl, and $CH_2F$;
wherein the stereochemical configuration at any stereocenter of the compound is R, S or a mixture of these configurations.

38. A composition comprising the compound of claim 1 and a pharmaceutically acceptable excipient.

39. A composition comprising the compound of claim 9 and a pharmaceutically acceptable excipient.

40. A composition comprising the compound of claim 19 and a pharmaceutically acceptable excipient.

* * * * *